(12) United States Patent
Kato et al.

(10) Patent No.: US 8,399,024 B2
(45) Date of Patent: Mar. 19, 2013

(54) WATER-INSOLUBLE MEDICINE

(75) Inventors: Hiroyuki Kato, Yokohama (JP); Isao Umeda, Yokohama (JP); Kazuo Watanabe, Tokyo (JP); Kazuya Hirata, Kawasaki (JP); Akio Ishiguro, Tokyo (JP); Tetsu Go, Chiba (JP)

(73) Assignee: Ebara Corporation, Tokyo (JP)

( * ) Notice: Subject to any disclaimer, the term of this patent is extended or adjusted under 35 U.S.C. 154(b) by 0 days.

(21) Appl. No.: 12/879,413

(22) Filed: Sep. 10, 2010

(65) Prior Publication Data

US 2011/0059183 A1 Mar. 10, 2011

Related U.S. Application Data

(63) Continuation of application No. 11/748,808, filed on May 15, 2007, now abandoned.

(30) Foreign Application Priority Data

May 15, 2006 (JP) .................. 2008-135677

(51) Int. Cl.
  *A61K 9/14* (2006.01)
  *A61K 31/44* (2006.01)
  *A61K 9/127* (2006.01)
  *C21C 1/00* (2006.01)

(52) U.S. Cl. ............ 424/489; 514/283; 514/2; 977/906; 266/202; 424/450

(58) Field of Classification Search .................. 424/489, 424/450; 514/283, 2; 977/906; 266/202
See application file for complete search history.

(56) References Cited

U.S. PATENT DOCUMENTS

| | | | |
|---|---|---|---|
| 4,045,565 A | 8/1977 | Le Pecq et al. | |
| 5,399,363 A | 3/1995 | Liversidge et al. | |
| 5,510,118 A * | 4/1996 | Bosch et al. | 424/489 |
| 2003/0137067 A1 | 7/2003 | Cooper et al. | |
| 2003/0211162 A1 | 11/2003 | Kerkhof | |
| 2004/0247624 A1* | 12/2004 | Unger et al. | 424/400 |
| 2004/0247660 A1 | 12/2004 | Singh | |
| 2006/0103060 A1* | 5/2006 | Kawakami et al. | 266/202 |
| 2006/0251584 A1 | 11/2006 | Nagare et al. | |
| 2006/0257489 A1 | 11/2006 | Kawakami et al. | |
| 2007/0114306 A1* | 5/2007 | Kawakami et al. | 241/1 |

FOREIGN PATENT DOCUMENTS

| | | |
|---|---|---|
| JP | 61-25041 | 2/1986 |
| JP | 05-125091 | 5/1993 |
| JP | 7-165562 | 6/1995 |

(Continued)

OTHER PUBLICATIONS

Wagner et al., Purification and characterization of phthalocyanines, Journey of Materials Science, 1982, 17, pp. 2781-2791.*

(Continued)

*Primary Examiner* — Ernst Arnold
*Assistant Examiner* — Hong Yu
(74) *Attorney, Agent, or Firm* — Oblon, Spivak, McClelland, Maier & Neustadt, L.L.P.

(57) ABSTRACT

A method of producing water-insoluble anti-cancer drug in the form of particulates, the method including preparing a water-insoluble anti-cancer drug having at least one multiple bond in the structure, and irradiating said water-insoluble anti-cancer drug with a laser beam having a wavelength of a low absorption portion in the vicinity of the foot of an absorption curve on the long wavelength side within the absorption band until said water-insoluble anti-cancer drug is formed into particulates having an average particle diameter of 50 to 200 nm.

9 Claims, 20 Drawing Sheets

FOREIGN PATENT DOCUMENTS

| | | |
|---|---|---|
| JP | 11-049679 | 2/1999 |
| JP | 2001-38246 | 2/2001 |
| JP | 2001-113159 | 4/2001 |
| JP | 2002-142763 | 5/2002 |
| JP | 2003-518038 | 6/2003 |
| JP | 2004-89890 | 3/2004 |
| JP | 2004-167316 | 6/2004 |
| JP | 2004-520157 | 7/2004 |
| JP | 2004-267918 | 9/2004 |
| JP | 2005-8524 | 1/2005 |
| JP | 2005-508939 | 4/2005 |
| JP | 2005-125204 | 5/2005 |
| JP | 2005-125258 | 5/2005 |
| JP | 2005-169386 | 6/2005 |
| JP | 2005-177596 | 7/2005 |
| JP | 2005-238124 | 9/2005 |
| JP | 2005-238342 | 9/2005 |
| JP | 2005-279328 | 10/2005 |
| JP | 2005-334782 | 12/2005 |
| JP | 2006-26503 | 2/2006 |
| JP | 2007-45674 | 2/2007 |
| WO | WO 02/056866 A1 | 7/2002 |
| WO | WO 2004/020086 A1 * | 3/2004 |
| WO | WO 2004/080586 A1 | 9/2004 |
| WO | WO 2005/049213 A1 | 6/2005 |
| WO | WO 2005/058480 A2 * | 6/2005 |
| WO | WO 2005/082521 A1 | 9/2005 |
| WO | WO 2005/092489 A1 | 10/2005 |

OTHER PUBLICATIONS

Yoshiaki Tamaki et al., "Tailoring nanoparticles of aromatic and dye molecules by excimer laser irradiation", Applied Surface Science, vol. 168, 2000, pp. 85-88.

Sanshiro Nagare et al., "Indomethacin nanoparticles directly deposited on the fluidized particulate excipient by pulsed laser deposition", Journal of Nanoparticle Research, vol. 6, 2004, pp. 589-593.

Bo Li, et al., "Enhancement of organic nanoparticle preparation by laser ablation in aqueous solution using surfactants", Applied Surface Science, vol. 210, 2003, pp. 171-176.

S. Nagare et al., "Reagglomeration mechanism of drug nanopartides by pulsed laser deposition", Solid State Ionics, vol. 172, 2004, pp. 243-247.

Kitamori et al., "Technology of microchemical chip and application thereof", the 1$^{st}$ edition, Maruzen, 2004, pp. 51, 52, 299, a front page and end page (with partial English Translation).

"The Merck Index An Encyclopedia Of Chemicals, Drugs, and Biologicals", 13TH Edition, Merck Research Laboratories Division of Merck & Co., Inc., 2001, 10 pages.

Atsushi Horiike, et al., "Topolsomerase Inhibitor: Irinotecan Hydrochloride and Etoposide", Journal of Clinical and Experimental Medicine, vol. 215, No. 5, pp. 324-332 (with Partial English Translation).

Yu Sakata, "VII Treatment of Gastric Cancer, and Treatment of Advanced and Recurrent Gastric Cancer/New Cancer Drug", Nipoppn Rinsho, vol. 59, Suppl. 4, pp. 386-392 (with Partial English Translation).

Mitsunori Hino et al., "DNA topoisomerase inhibitor", vol. 51, No. 12, 1993, 2 cover page and pp. 221-230 (with English Summary).

Anatoly N. Lukyanov, et al., "Micelles from polyethylene glycol/phosphatidylethanolamine conjugates for tumor drug delivery", Journal of Controlled Release 91 (2003) 97-102.

Apama Krishnadas, et al., "Sterically Stabilized Phospholipid Mixed Micelles: In Vitro Evaluation as a Novel Carrier for Water-Insoluble Drugs", Pharmaceutical Research, vol. 20, No. 2, Feb. 2003, pp. 297-302.

R.T. Liggins, et al., "Polyether-polyester diblock copolymers for preparation of paclitaxel loaded polymeric micelle formulations", Advanced Drug Delivery Reviews 54 (2002) 191-202.

Debora G. Rodrigues, et al., "Use of a cholesterol-rich emulsion that binds to low-density lipoprotein receptors as a vehicle for paclitaxel", Journal of Pharmacy and Pharmacology, 2002, 54: 765-772.

Panayiotis P. Constantinides, et al., "Formulation Development and Antitumor Activity of a Filter-Sterilizable Emulsion of Paclitaxel", Pharmaceutical Research, vol. 17, No. 2, 2000, pp. 175-182.

Pei Kan, et al., "Development of nonionic surfactant/phospholipid o/w emulsion as a paclitaxel delivery system" Journal of Controlled Release, 58 (1999) 271-278.

Rainer Kunstfeld, et al., "Paclitaxel Encapsulated in Cationic Liposomes Diminishes Tumor Angiogenesis and Melanoma Growth in a "Humanized" SCID Mouse Model", The Journal of Investigative Dermatology, vol. 120, No. 3, Mar. 2003, pp. 476-482.

Fjällskog M.L., et al., "Is Cremophor EL, solvent for paclitaxel, cytotoxic?" LANCET, Oct. 2, 1993, vol. 342, p. 873.

A. Chanan-Khan, et al., "Complement activation following first exposure to pegylated liposomal doxorubicin (Doxil®): possible role in hypersensitivity reactions", Annals of Oncology 14: 1430-1437, 2003.

Simone Cesaro et al., "Allergic reaction to the liposomal component of liposomal amphotericin B", Support Care Cancer (1999), 7:284-286.

Raymond B. Weiss et al., "Hypersensitivity Reactions From Taxol", Journal of Clinical Oncology, vol. 8, No. 7, Jul. 1990: pp. 1263-1268.

Hang Lu et al., "Photochemical reactions and on-line UV detection in microfabricated reactors", Lab on a Chip, vol. 1, 2001, pp. 22-28.

Daniele Demarquay, et al., "The homocamptothecin BN 80915 is a highly potent orally active topoisomerase I poison", Anti-Cancer Drugs, vol. 12, 2001, pp. 9-19.

Chris H. Takimoto, et al., "Clinical applications of the camptothecins", Biochimica et Biophysica Acta, vol. 1400, 1998, pp. 107-119.

* cited by examiner

RETENTION TIME: 6.08 MINUTES (SPREADING SOLVENT: ETHANOL)
LASER IRRADIATION (100 mJ/cm², 10 SECONDS)

HISTOGRAM OF PARTICLE DIAMETER DISTRIBUTION OF ELLIPTICINE FOLLOWING LASER IRRADIATION 100 mJ/cm², 10 SECONDS FROM IRRADIATION
(NUMBER OF SAMPLES: 119, CV VALUE: 20%)

FIG. 14B
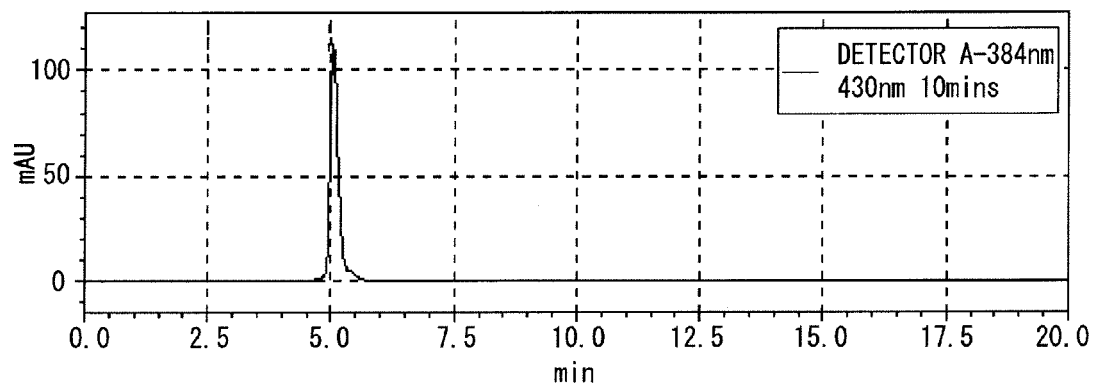
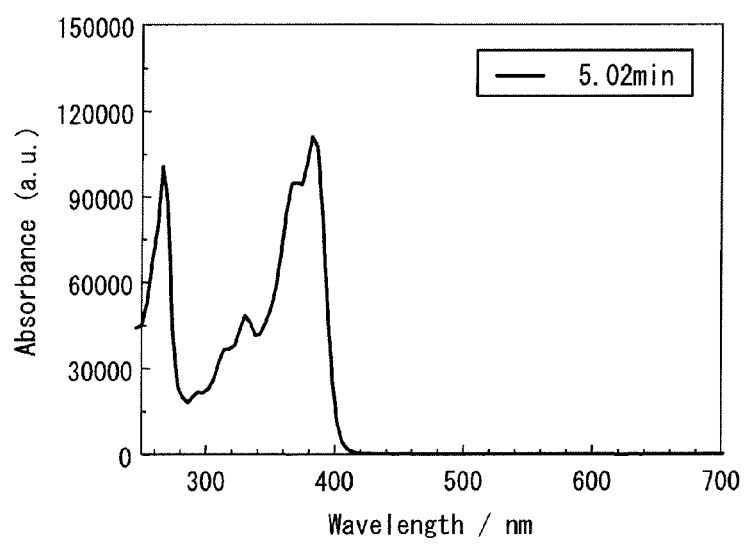

FIG. 15
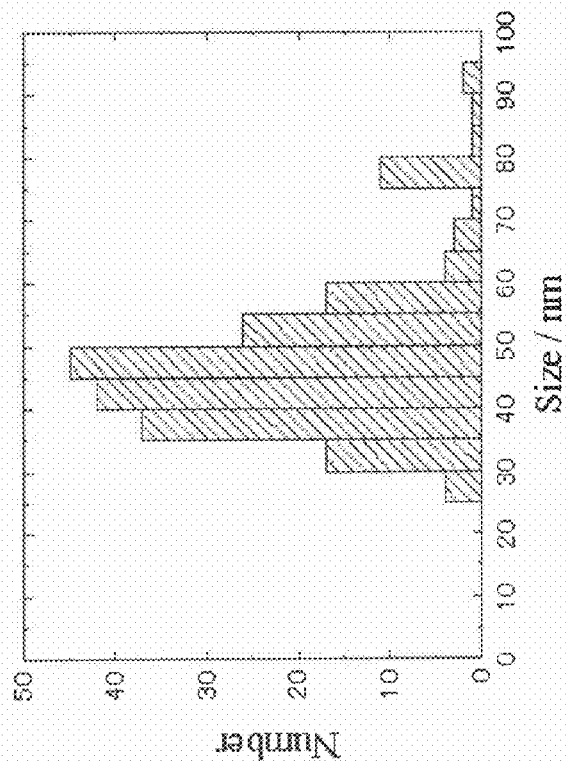
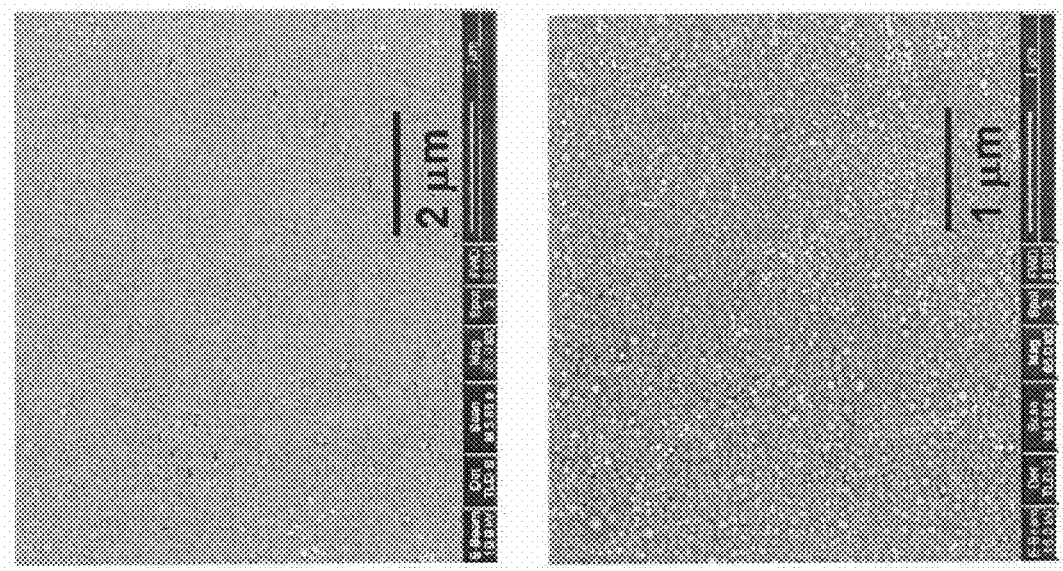

FIG. 18A
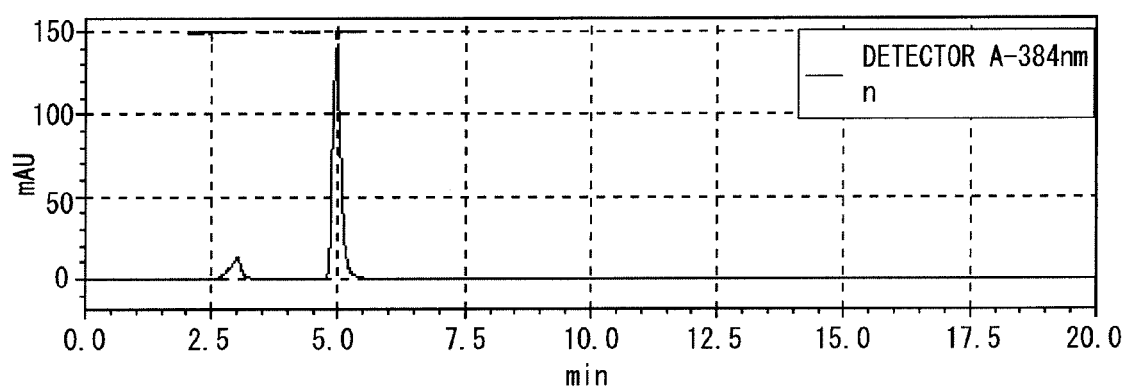
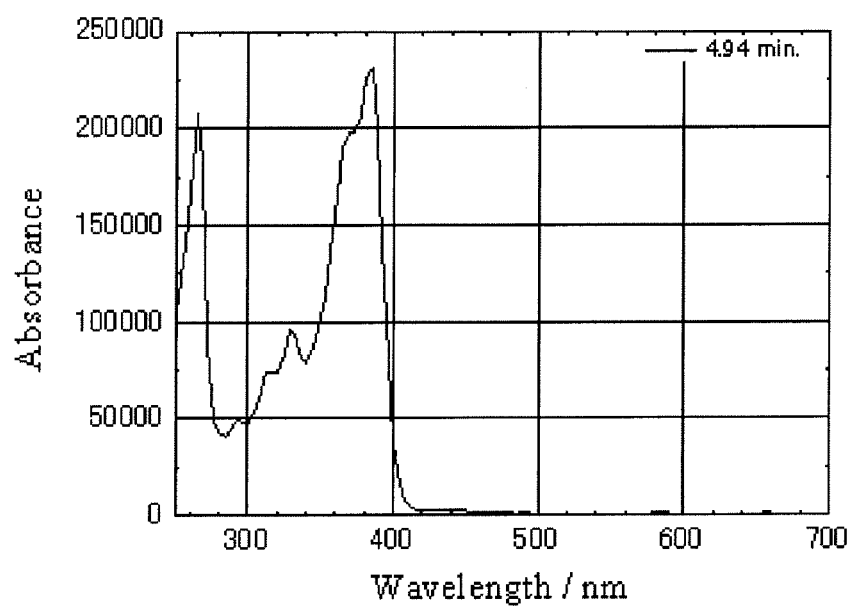

FIG. 19
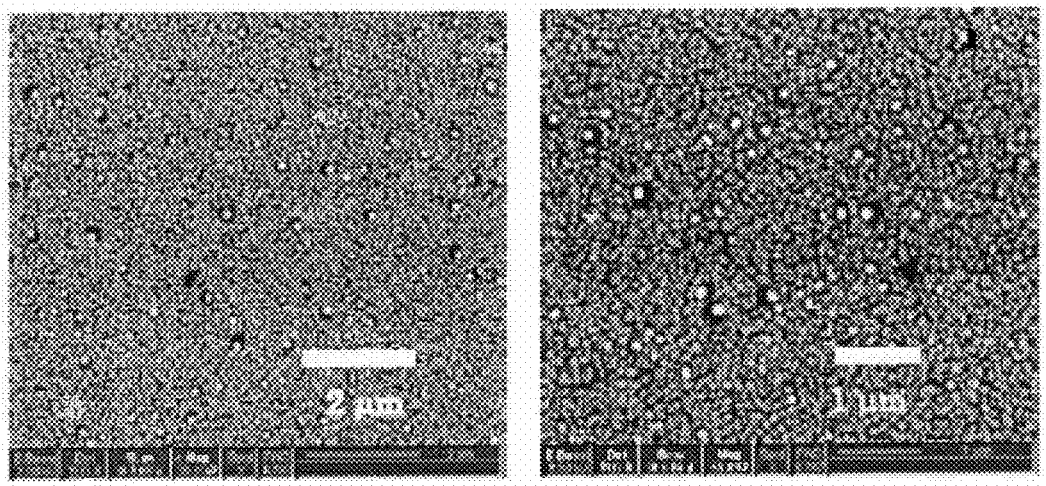
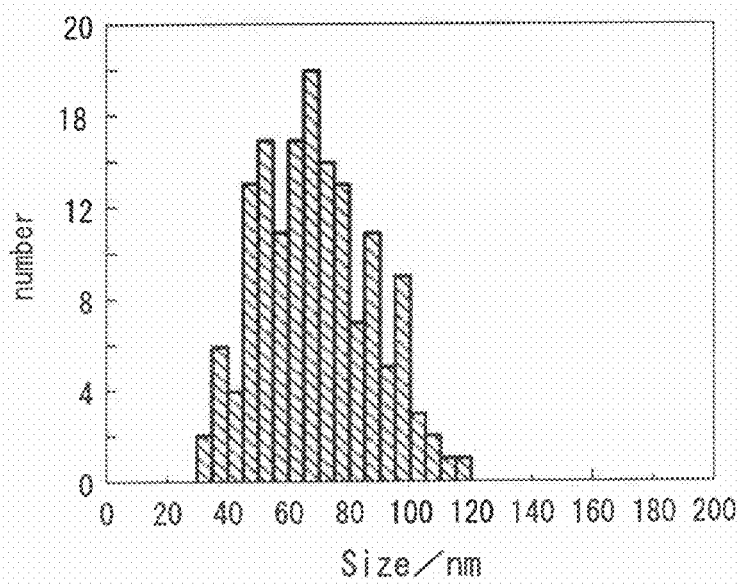

WATER-INSOLUBLE MEDICINE

CROSS-REFERENCE TO RELATED APPLICATIONS

This application is a continuation of and claims benefit of priority from U.S. application Ser. No. 11/748,808, filed May 15, 2007, which claims the benefit of priority from Japanese Patent Application No. 2006-135677, filed May 15, 2006, the entire contents of each of which are incorporated herein by reference.

BACKGROUND OF THE INVENTION

1. Field of the Invention

The present invention relates to a fine-particulate, water-insoluble medicine, and a complex of the same with a polymer electrolyte. More particularly, the present invention is related to a medicine in the form of ultrafine particles obtained by irradiating a laser beam onto particles, and an ultrafine particle-polymer electrolyte complex.

2. Description of Related Art

Medicines insoluble to solvents, such as anticancer drugs, are insoluble to water and are hardly absorbed by cells, so that the bioavailability thereof is low. Therefore, when these water-insoluble medicines are used for injection, a solubilizer is often added for the purpose of enhancing the water solubility of the medicines to thereby improve the bioavailability thereof. However, this solubilizer has toxicity problems.

For improving the intake of the water-insoluble medical drugs by cells without using a solubilizer, the size of the drugs can be reduced to ultrafine particles which can pass through the cell membrane of the affected part. The size of ultrafine particles which can pass through a cell membrane is considered to be 200 nm or less.

As an organic substance is expected to exhibit interesting improvement and changes in properties by size-reduction, various methods for forming ultrafine particles of an organic compound have been proposed. For example, a method has been disclosed in which an organic compound dispersed in a solvent is irradiated with a laser beam to thereby form ultrafine particles of the organic compound (for example, see Japanese Unexamined Patent Application, First Publication No. 2001-113159). In the method disclosed in Japanese Unexamined Patent Application, First Publication No. 2001-113159, an organic compound is irradiated with a beam having a wavelength within the absorption band wavelength, so that thermal stress cracking is caused by linear optical absorption at a relatively weak chemical bond within the molecular structure, thereby forming ultrafine particles. However, simultaneously with the formation of ultrafine particles, it is highly possible that electronic excitation occurs in some portions of the organic compound to cause a photochemical reaction, such that the organic compound decomposes. Especially when the organic compound is a medical drug to be administered into a body, there is a danger that the decomposition product may harmfully affect the body, and hence, such a serious situation must be avoided.

For improving the method disclosed in Japanese Unexamined Patent Application, First Publication No. 2001-113159, a method for forming ultrafine particles has been proposed in which the organic compound within the liquid to be treated is irradiated with a laser beam having a wavelength longer than the absorption band (for example, see Japanese Unexamined Patent Application, First Publication No. 2004-267918). Further, a method for forming ultrafine particles has been proposed in which a bulk crystal of an organic compound dispersed in a poor solvent is irradiated with a very short pulsed laser to induce ablation by non-linear absorption, thereby pulverizing the bulk crystal (for example, see Japanese Unexamined Patent Application, First Publication No. 2005-238342).

In these methods, crude particles of an organic compound dispersed in a solvent within a transparent vessel are externally irradiated with a laser beam having a wavelength longer than the absorption band or a very short pulsed laser, thereby pulverizing the organic compound within the solvent. These methods enable formation of ultrafine particles of an organic compound under relatively mild conditions, as compared to the method in which a beam having a wavelength within the absorption band is linearly absorbed. Therefore, in these methods, there is less danger of the organic compound decomposing, and these methods were considered to be suitable for formation of ultrafine particles of insoluble organic compounds in small amounts, especially medical drugs.

However, although the principle of pulverization by laser beam irradiation is assumed to be thermal stress cracking caused by short-term heating by pulse energy, the laser energy absorption properties of the drug and setting of the laser irradiation period become important parameters for forming ultrafine particles of the drug without causing deterioration. In a batchwise method, a laser beam is irradiated onto the drug in a state where the drug is dispersed in solvent within a vessel, or in a state where the drug is being stirred in the vessel. Therefore, in a batchwise manner, it was difficult to control various conditions, such as setting the laser beam irradiation period and uniformly irradiating the laser beam onto the dispersed particles. For example, certain particles are irradiated with the laser beam many times, whereas other particles are not irradiated at all. Therefore, formation of ultrafine particles of a drug which have a uniform particle size within a predetermined range and which are free from deterioration so as to exhibit high bioavailability, has not been achieved at an industrial scale.

SUMMARY OF THE INVENTION

An object of the present invention is to provide a particulate, water-insoluble medicine which has a uniform particle size within a predetermined range and which is unchanged in a drug effect so as to exhibit high bioavailability, and a complex of such particulate, water-insoluble medicine with a polymer electrolyte.

In this situation, the inventors have performed extensive and intensive studies in view of solving the above-mentioned problems. As a result, they found that the above-mentioned problems can be solved by using a technique for forming ultrafine particles by the laser ablation method, while controlling the conditions for the laser beam irradiation in detail. Based on this finding, the present invention has been realized.

Accordingly, the present invention provides the following items 1 to 8:

1. A water-insoluble medicine in the form of particulates, having an average particle diameter of 50 to 200 nm.
2. The water-insoluble medicine according to item 1 above, which has at least one multiple bond in the structure.
3. The water-insoluble medicine according to item 1 or 2 above, which is an anti-cancer drug.
4. The water-insoluble medicine according to item 3 above, wherein the anti-cancer drug is a camptothecin derivative.
5. The water-insoluble medicine according to item 3 above, wherein the anti-cancer drug is an ellipticine derivative.
6. The water-insoluble medicine according to item 3 above, wherein the anti-cancer drug is a podophyllotoxin derivative.

7. A particulate complex of the water-insoluble medicine of any one of items 1 to 6 above with a polymer electrolyte, having an average particle diameter of 50 to 250 nm.

8. The particulate complex according to item 7 above, wherein the polymer electrolyte is at least one member selected from the group consisting of: biocompatible polymers including protamine, gelatin A, collagen, albumin, casein, chitosan, poly-(L)-lysine, carboxymethyl cellulose, alginate, heparin, hyaluronic acid, chondroitin sulfate, gelatin B, carageenan, dextran sulfate, and poly-(L)-glutamic acid; biopolymers including biodegradable polymers, DNA, RNA, enzymes and antibodies; synthesized polymers including polymethacrylic acid, polydiaryldimethylammonium; and polymers in which such synthesized polymers are crosslinked with an appropriate linker.

The medicine of the present invention in the form of ultrafine particles, and a complex of the same with a polymer electrolyte can be manufactured as a colloidal dispersion which is stable and free from contamination, so that they can be used for various injectable formulations. Thus, the medicine of the present invention in the form of ultrafine particles, and a complex of the same with a polymer electrolyte can be directly injected into a blood vessel. In an oral administration, only a small amount of the drug can be delivered to the inside of the body because of the low absorbability of the drug due to its water insolubility. Further, in an oral administration, the drug is deteriorated by gastric juices and enzymes, such that the drug effect is impaired. On the other hand, the medicine of the present invention is injected into a blood vessel, and the medicine is transferred at an extremely high speed, so that the delivery of the medicine from the administration part to the target part is extremely fast.

The medicine of the present invention in the form of ultrafine particles, especially an anti-cancer drug, and a complex of the same with a polymer electrolyte hardly pass through normal vascular endothelial cells which have relatively narrow spaces between the tissues, but are capable of passing through vascular endothelial cells extending from tumor cells in which the spaces between the tissues of the vascular endothelial cells are relatively large, so as to be absorbed by the tumor cells. Thus, the medicine of the present invention in the form of ultrafine particles and a complex of the same with a polymer electrolyte hardly pass through normal vascular endothelial cells during the delivery thereof to the target part, so that normal cells are not harmfully affected. Further, the dose of the drug can be suppressed to a small amount, so that strong side-effect of the anti-cancer drug can be suppressed.

In addition, the medicine of the present invention in the form of ultrafine particles, especially an anti-cancer drug, and a complex of the same with a polymer electrolyte has a high probability of being absorbed by tumor cells, as compared to conventional drugs. Therefore, the medicine and the complex are hardly affected by individual difference in improvement of bioavailability and absorption of the drug.

BRIEF DESCRIPTION OF THE DRAWINGS

FIG. 14B shows a chromatogram of supernatant of SN-38 suspension following laser irradiation (spreading solvent: ethanol) and results of HPLC analysis.

FIG. 15 shows respective SEM images of SN-38 following laser irradiation and centrifugal separation (2,000 rpm, 10 minutes), and a histogram of particle diameter distribution (number of samples: 200, average particle diameter: 46 nm, CV value: 22%).

FIG. 18A is a chromatogram of 10-hydroxy-camptothecin prior to laser irradiation (spreading solvent: ethanol) and results of HPLC analysis.

FIG. 19 shows respective SEM images of 10-hydroxy-camptothecin following laser irradiation and centrifugal separation (2,000 rpm, 10 minutes), and a histogram of particle diameter distribution (number of samples: 150, average particle diameter: 68 nm, CV value: 25%).

REFERENCE NUMERALS

Figure 1:
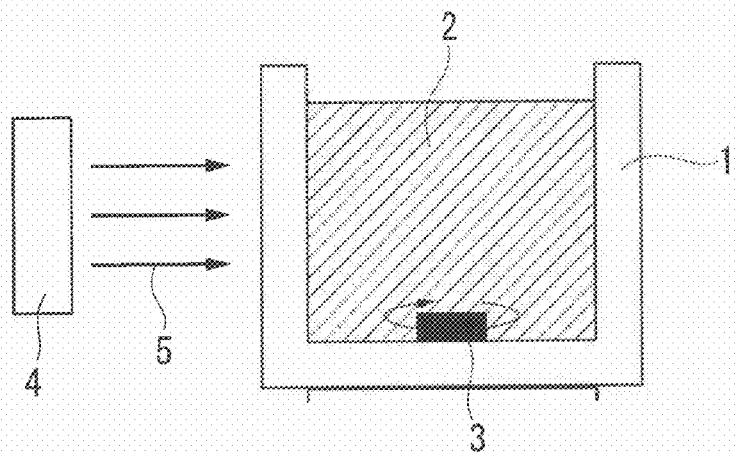
FIG. 1 is a general view of an apparatus for forming ultrafine particles in a batchwise manner, which was used for manufacturing the particulate, water-insoluble medicine and complex according to the present invention.

1 Vessel
2 Suspension
3 Stirrer
4 Laser beam source
5 Laser beam
6 Light source
40 Pump (flow device)
50 Microflow-channel introductory part
60 Microflow channel
64 Transition part
100 Apparatus for forming ultrafine particles
120 Polymer membrane-shell coating part
122a Microflow channel for ultrafine-particle suspension
122b Microflow channel for polymer electrolyte solution
122c Merged microflow channel
124 Tank for polymer electrolyte solution
140 Complex collecting vessel

PREFERRED EMBODIMENTS OF THE PRESENT INVENTION

In the present invention, particles of a medicine are size-reduced to ultrafine particles by irradiating with a laser beam. In the present invention, the medicine to be size-reduced to ultrafine particles may be a solid powder having an arbitrary size and shape, such as a synthesized crude powder. However, in view of easily forming ultrafine particles, enhancing the efficiency of the formation of ultrafine particles and easily rendering the size of the ultrafine particles of the medicine uniform, it is preferable that the particles of the medicine be pulverized to fine particles having an average particle diameter within a narrow range, for example, from 1 to 100 μm. The pulverization can be conducted by any conventional method.

In the present invention, the medicine to be size-reduced to ultrafine particles is a water-insoluble, particulate drug. In the present invention, the term "water-insoluble" refers to the solubility as prescribed in the Japanese pharmacopoeia, which is defined as being "extremely hard to dissolve in water" or "hardly dissolved in water".

Further, in the present invention, the medicine to be size-reduced to ultrafine particles preferably has at least one multiple bond in the structure. The reason for this is that, when particles of the medicine are irradiated with a laser beam, the multiple bond portions easily absorb the laser beam, and local temperature elevation is rapidly caused at the portions where the beam was absorbed. This temperature elevation occurs instantly following the irradiation with the laser beam, so that temperature difference is generated between the portions where the beam was absorbed and the portions where the beam was not absorbed, and hence, breaking of the particles occurs. In the present invention, the term "multiple bond" refers to a conjugated or non-conjugated double bond or triple bond.

Further, in the present invention, the medicine to be size-reduced to ultrafine particles refers to a medical product as prescribed by the Pharmaceutical Affairs Law, or a candidate compound for a medicine which has been phased out at the human clinical trial stage, or which is at a developmental phase in the human clinical trial. Examples of water-insoluble medicines include anti-caner drugs, antifungal drugs, vitamins, painkillers and anti-inflammatory agents.

It is particularly desirable that the particulate, water-insoluble medicine of the present invention be an anti-cancer drug. The reason for this is as follows. It is considered that the spaces existing between tissues of vascular endothelial cells extending from tumor cells are large as 50 nm or more, which is larger than the spaces existing between tissues of normal vascular endothelial cells. Therefore, a particulate, water-insoluble anti-cancer drug having an average particle diameter of 50 to 200 nm can be suited for various injectable formulations, since such anti-cancer drug can easily pass vascular endothelial cells extending from tumor cells, but not normal vascular endothelial cells.

In the present invention, the term "anti-cancer drug" refers to a medical product which is prescribed by the Pharmaceutical Affairs Law and which exhibits anti-cancer activities, or a candidate compound for a medicine exhibiting anti-cancer activities, which has been phased out at the human clinical trial stage, or which is at a developmental phase in the human clinical trial.

Examples of anti-cancer drugs usable in the present invention include camptothecin and derivatives thereof, ellipticine and derivatives thereof, and podophyllotoxin and derivatives thereof. The general structural formulas of these compounds are shown below.

Camptothecin and derivatives thereof having a structure represented by the structural formula shown below:

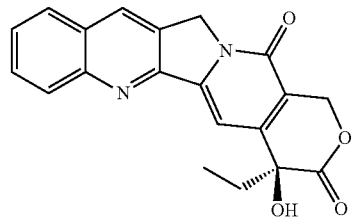 [SMILES: CC[C@@]1(O)C(=O)OCc2c1cc1n(c2=O)Cc2cc3ccccc3nc2-1]

Ellipticine and derivatives thereof having a structure represented by the structural formula shown below:

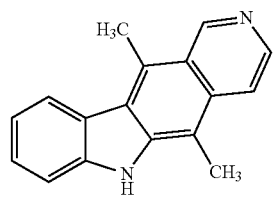 [SMILES: Cc1c2ccncc2c(C)c2c1[nH]c1ccccc12]

Podophyllotoxin and derivatives thereof having a structure represented by the structural formula shown below:

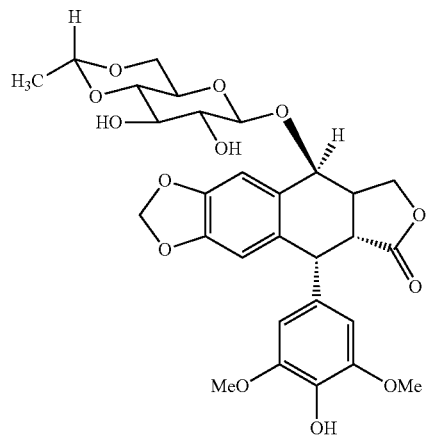

Specific examples of camptothecin derivatives include 4(s)-ethyl-4-hydroxy-1H-pyrano[3',':6,7]indolizino[1,2-b]quinoline-3,14(4H,12H)-dione(camptothecin), 7-ethyl-10-hydroxycamptothecin (SN-38), 9-aminocamptothecin, 9-nitrocamptothecin 5(R)-ethyl-9,10-difluoro-1,4,5,13-tetrahydro-5-hydroxy-3H,15H-oxepino[3',':6,7]indolizino[1,2-b]quinoline-3,15-dione (BN-80915) [Anti-cancer Drugs (2001), 12(1), 9-19], and (9S)-9-ethyl-9-hydroxy-1-pentyl-1H,12H-pyrano [3'',4'':6,7']indolizino[1',2':6,5]pyrido[4,3,2-de]quinazoline-10,13(9H,15H)-dione [Cancer Chemotherapy and Biotherapy: Principle and Practice, second edition, Lippincott-Ravenmeans, p. 463-484, (b) Biochim. Biophys. Acta (1998), 1400(1-3), 107-119], although the camptothecin derivatives are not limited to these examples.

Specific examples of ellipticine derivatives include ellipticine, 9-hydroxy-ellipticine and T-215 (TANABE SEIYAKU Co. Ltd.), although the ellipticine derivatives are not limited to these examples.

Specific examples of podophyllotoxin derivatives exhibiting anti-cancer activities include podophyllotoxin, etoposide and teniposide, although the podophyllotoxin derivatives are not limited to these examples.

Water or alcoholic solution for dispersing the particulate drug hardly dissolves the particulate drug to be size-reduced, does not adversely affect human bodies, and does not absorb laser beams. Examples of alcohols usable in the present invention include ethyl alcohol, glycol and glycerol. The alcoholic solution is generally an aqueous solution of 5% by weight or less of an alcohol.

The particulate, water-insoluble medicine of the present invention has an average diameter of 50 to 200 nm. The average diameter of the particles is a value obtained by measuring the diameter of each particle using a microscope provided with a scale, and dividing the sum of the particle diameters by the number of particles.

The particulate, water-insoluble medicine is manufactured by suspending a particulate anti-cancer drug in water or an alcoholic solution, and irradiating the suspended drug with a laser beam to form ultrafine particles thereof. More specifically, the particulate, water-insoluble medicine is manufactured as follows. Firstly, water or an alcoholic solution is charged into a vessel 1 shown in FIG. 1, and a particulate drug is mixed therewith to form a suspension 2. The concentration of the suspension 2 varies depending on the type and size of the particulate drug mixed, but is generally from 1 to 10 mg/ml. Further, the vessel 1 may have any shape as long as the face to be irradiated with the laser beam is planar, but it is preferable that the vessel 1 is substantially cuboid, and the size of the vessel 1 may be appropriately selected depending on the amount of the drug to be treated. The material for the vessel 1 need not be transparent as long as it is capable of transmitting a laser beam, and any material capable of sustaining the laser beam irradiation may be used. In general, the material for the vessel 1 is quartz or glass.

The particulate medicine of the present invention which is insoluble in water or the alcoholic solution and which has an average diameter of 50 to 200 nm tends to agglomerate by the surface energy thereof. Therefore, the ultrafine particles may be subjected to an electrostatic interaction or hydrophobic interaction with a polymer electrolyte having a charge opposite to the ultrafine particles to form a complex, so as to manufacture the particulate medicine in the form of a colloidal dispersion which is stable and free from contamination.

In the present invention, the term "complex" refers to ultrafine particles coated with one layer of a polymer electrolyte. A complex preferably has an average diameter of 50 to 250 nm.

The manufacture of a complex is influenced by the ultrafine particles as the core substance, and various conditions such as the reaction period, concentration of the suspension and pH of the suspension are determined in detail, depending on the core substance. Therefore, the manufacture of a complex cannot be defined in a single uniform way.

The thus manufactured complex of the particulate medicine with a polymer electrolyte can be used for various injectable formulations, and can be directly injected into a blood vessel. In an oral administration, only a small amount of the drug can be delivered to the inside of the body because of the low absorbability of the drug due to its water insolubility. Further, in an oral administration, the drug is deteriorated by gastric juices and enzymes, such that the drug effect is impaired. On the other hand, the medicine of the present invention is injected into a blood vessel, and the medicine is transferred at an extremely high speed, so that the delivery of the medicine from the administration part to the target part is extremely fast.

The ultrafine particles formed by the laser irradiation tend to agglomerate due to the surface energy thereof. That is, when the concentration of the ultrafine particles within the suspension 2 is too high, agglomeration is likely to occur. Therefore, the concentration of the ultrafine particles within the suspension 2 cannot be rendered too high. For this reason, it is preferable that a polymer electrolyte having a charge opposite to the ultrafine particles be added to the suspension 2 prior to irradiation of the laser beam. In this manner, the ultrafine particles form a complex with the polymer electrolyte. The complex does not have a surface energy as high as the ultrafine particles. Therefore, the particles of the complex do not agglomerate with each other, and are stably suspended in water or a diluted alcohol. In other words, by adding a polymer electrolyte to the suspension 2 in advance, the concentration of the drug mixed with the suspension 2 can be enhanced, and the amount of the drug to be treated can be increased. As the polymer electrolyte to be added to the suspension 2 for this purpose, one or more types of polymer electrolytes may be used. The concentration of the polymer electrolyte to be added is generally from 1 to 10%.

The polymer electrolyte usable in the present invention is a polymer having an ion-dissociable group which is typically a polymer chain component or a substituent. In general, the number of the ion-dissociable groups within the polymer electrolyte is a number such that the polymer following the dissociation of the ion-dissociable groups becomes water-soluble. In view of this, it is considered that the polymer electrolyte includes ionomers which have ion groups with a concentration insufficient to exhibit water solubility, but has an electric charge sufficient for initiating self-assembly. The polymer electrolyte is classified into polyacids and polybase, depending on the type of the ion-dissociable group. From a polyacid, a polyanion is generated by elimination of proton upon dissociation, and the polyanion may be an inorganic polymer or an organic polymer. Examples of polyacids include polyphosphoric acid, polyvinylsulfuric acid, polyvinylsulfonic acid, polyvinylphosphonic acid, polyacrylic acid, and salts thereof.

A polybase includes a group which is capable of taking up protons for example by formation of salt by reacting with an acid. Examples of polybases having an ion-dissociable group on the chain position or side-chain position include polyethyleneimine, polyvinylamine and polyvinylpyridine. The polybase forms a polycation by taking up protons.

Examples of polymer electrolytes suitable for use in the present invention include biocompatible polymers, biodegradable polymers, biopolymers and synthesized polymers.

A biocompatible polymer is a polymer which is compatible with biotissues and organ system without causing toxicity, damage, or rejection. A biodegradable polymer is a generic term of polymers which are decomposed in vivo or decomposed by action of microbes, and are decomposed into water, carbon dioxide, methane and the like by hydrolysis. A biopolymer is a generic term of polymeric compounds which are synthesized in vivo.

Specific examples of biocompatible polymers include protamine, gelatin A, collagen, albumin, casein, chitosan, poly-(L)-lysine, carboxymethyl cellulose, alginate, heparin, hyaluronic acid, chondroitin sulfate, gelatin B, carageenan, dextran sulfate, and poly-(L)-glutamic acid. Specific examples of biodegradable polymers include DNA, RNA, enzymes and antibodies. Specific examples of synthesized polymers include polymethacrylic acid, polydiaryldimethylammonium, and polymers in which such synthesized polymers are crosslinked with an appropriate linker. However, polymer electrolytes are not limited to these examples.

The electric charge of the above-mentioned polymer electrolyte can be changed to a positive charge or negative charge by varying the pH. Therefore, the polymer electrolyte for use changes, depending on various conditions.

The thus prepared suspension 2 is stirred with a stirrer 3, which is preferably a magnetic stirrer, to thereby uniformly disperse the drug and the polymer electrolyte.

The drug dispersed in water or a diluted alcohol is irradiated with a laser beam 5 generated from a laser source 4, which has a wavelength within the absorption band. The laser source 4 may be a laser source capable of continuously generating a laser beam with a substantially constant intensity, or may be a laser source capable of intermittently generating a laser beam such as a pulsed laser beam.

The laser beam generated from the light source 4 may be selected depending on the absorption wavelength of the drug to be size-reduced. Examples of the laser beam include an ultraviolet laser beam, a visible laser beam, a near-infrared laser beam or an infrared laser beam. Examples of ultraviolet laser beams include excimer lasers (193 nm, 248 nm, 308 nm, 351 nm), a nitrogen laser (337 nm), and the third and fourth harmonics of a YAG laser (355 nm, 266 nm). Examples of visible laser beams include the second harmonic of a YAG laser (532 nm), an Ar ion laser (488 nm or 514 nm), and dye lasers. Examples of near-infrared lasers include various semiconductor lasers, a titanium-sapphire laser, a YAG laser and a glass laser. Further, by using any of the above-exemplified lasers with an optical parametric oscillator, a light ray having a desired wavelength within the range of ultraviolet to infrared may be oscillated.

Figure 2:
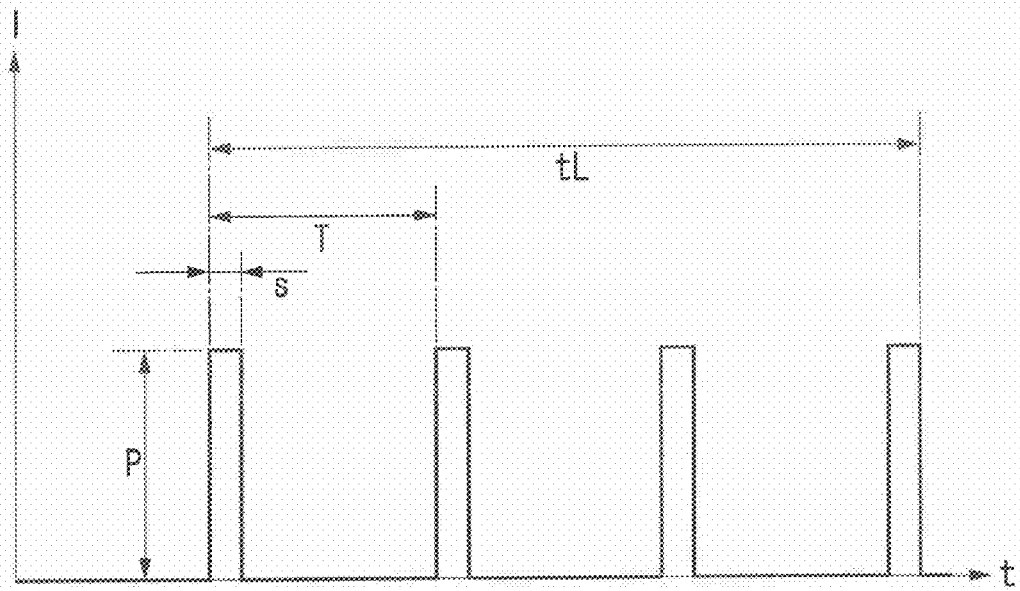
FIG. 2 is a graph showing the pulse width and intensity of the laser beam generated from the light source 10.

The laser beam generated from the light source 4 is preferably a pulsed laser beam. FIG. 2 is a graph showing the pulse width and intensity of the laser beam generated from the light source 4. In the graph shown in FIG. 2, the horizontal axis indicates time, and the vertical axis indicates the excitation light intensity of the laser beam generated from the light source 4. As shown in FIG. 2, the laser beam generated from the light source 4 is a pulsed laser beam. That is, the light source 4 generates a laser beam intermittently, so as to alternately repeat an on-state in which a laser beam is generated and an off-state in which a laser beam is not generated. It is particularly desirable to use a laser beam in which the intensity changes in a pulsewise manner. Hereafter, one pulse of a laser beam is referred to as a "pulsed beam". When a pulsed laser beam is used, one pulsed beam effects one irradiation.

The excitation light intensity P of the laser beam generated from the light source 4 is preferably from 1 to 1,000 mJ/cm$^2$, more preferably 30 to 300 mJ/cm$^2$. Further, the pulse period T between a pulsed beam and a subsequent pulsed beam (adjacent pulsed beams) is preferably from 0.1 to 1,000 Hz. Here, a "pulse period" means the period from the start of a pulsed beam to the start of a subsequent (adjacent) pulsed beam, or the period from the end of a pulsed beam to the end of a subsequent (adjacent) pulsed beam. Furthermore, the pulse width s of respective pulsed beams is preferably from $10^{-15}$ to $10^{-6}$ seconds. Here, a "pulse width" means the period from the start of a pulsed beam to the end of the pulsed beam.

When a pulsed laser beam is used, one irradiation of the drug is effected by one pulsed beam. In the present specification, the period during which a laser beam can be irradiated onto a target drug is referred to as "irradiation period tL". As shown in FIG. 2, when the irradiation period tL is long, it includes both of the on- and off-states of the pulsed laser beam. In the off-state, no laser beam is generated, whereas in the on-state, a laser beam is generated and irradiated onto a target drug. Thus, even when a certain period includes an off-state, that period is regarded as the irradiation period tL if it also includes an on-state in which a laser beam can be irradiated onto a target drug.

More specifically, when a target drug is allowed to flow into the irradiation region of the laser beam, remain in the irradiation region for a long period, and then come out of the irradiation region, the drug gets irradiated with a pulsed beam a plurality of times. That is, when the drug is allowed to flow in this manner, the above-mentioned irradiation period tL is regarded as the period during which the target drug is present in the irradiation region of the laser beam. As described above, ultrafine particles of the drug can be formed by irradiating the drug with a laser beam. For forming ultrafine particles having a desired size, the number of irradiations of the drug with a pulsed beam can be determined. The number of irradiations with a pulsed beam can be changed by adjusting the above-mentioned pulse period T, the flow rate of the drug, etc. Thus, in the irradiation region of the laser beam, the drug is irradiated with a pulsed beam at least once. The irradiation region of the laser beam is the region where the laser beam is irradiated during the on-state.

As described above, with respect to the irradiation period, it is preferable that a pulsed beam of a short period in the order of nano seconds be irradiated a plurality of times. Further, by changing the above-mentioned pulse width s, the particle diameter of the ultrafine particles of the drug can be controlled.

As in the present embodiment, when ultrafine particles are formed in a batchwise manner using a stirring vessel, the drug is irradiated with the laser beam a plurality of times while stirring. For this reason, the drug may be irradiated with the laser beam too many times, such that the formed ultrafine particles have an average diameter of less than 50 nm, or that the drug may be deteriorated. Therefore, the total irradiation period of the laser beam is an important factor.

The total irradiation period of the laser beam varies depending on the stirring rate, the size of the drug, the laser beam source, the pulse width, the beam intensity, and the like, but is generally from a few seconds to a few minutes.

When a polymer electrolyte is not added in advance, it is necessary that a polymer electrolyte be added immediately after the stop of the laser beam irradiation to form complexes, thereby stably suspending the ultrafine particles in water or the diluted alcohol.

The thus obtained colloidal solution containing the complexes may be either diluted with an appropriate solvent or concentrated, so that it becomes usable as an injection having a desired concentration.

Further, when the complexes are desired to be obtained in the form of a solid, the colloidal solution is passed through a filter to separate the solid contents, followed by washing, and optionally drying. Alternatively, the water or diluted alcohol within the colloidal solution may be vaporized to collect the solid contents, followed by washing, and optionally drying. In the latter case, as the solvent, an alcohol, liquid nitrogen or liquid helium is preferable.

Hereinabove, explanation has been given of a method for manufacturing the medicine of the present invention in a batchwise manner. Next, explanation is given of a method for manufacturing the medicine of the present invention in a continuous manner.

Figure 3:
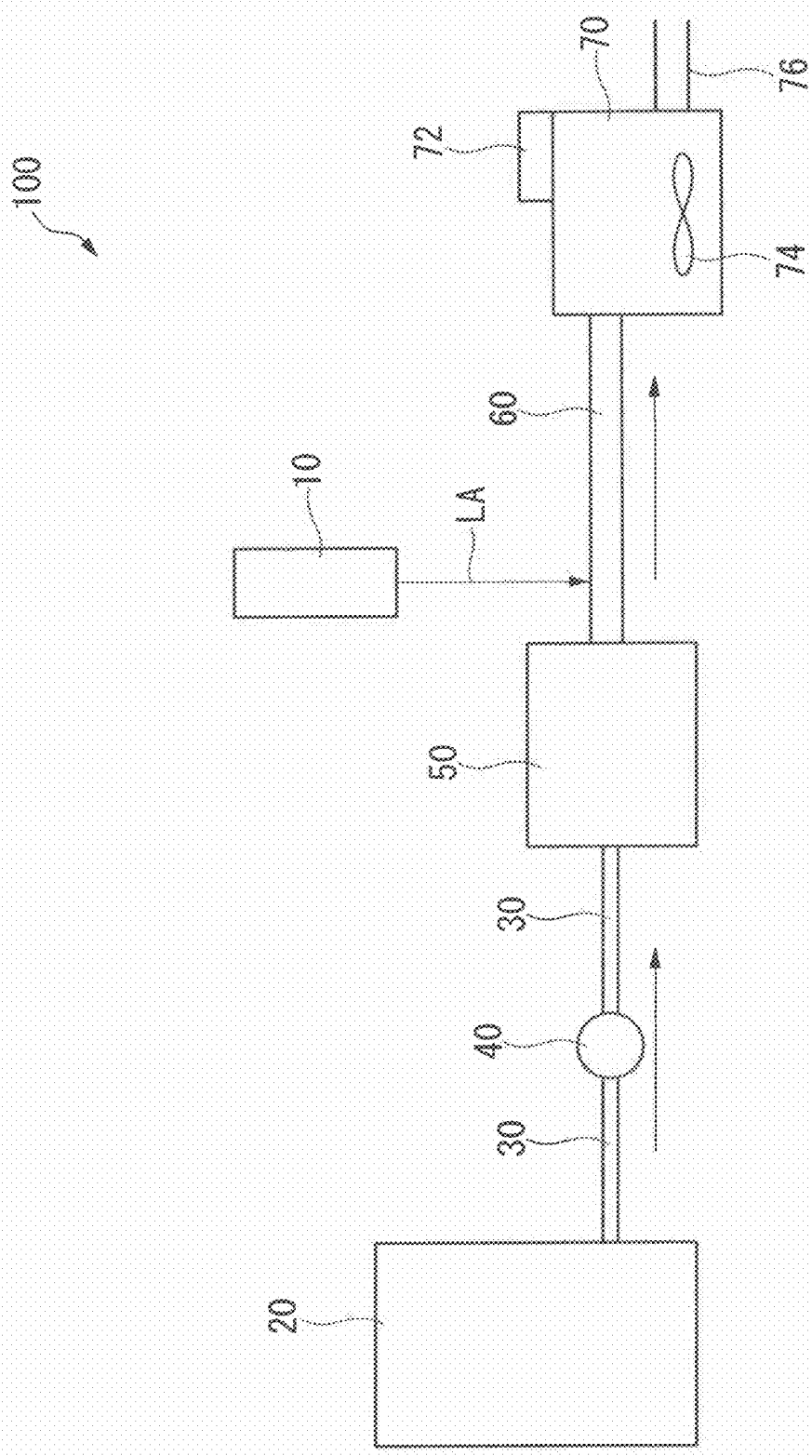
FIG. 3 is a general view of an apparatus for forming ultrafine particles in a continuous manner, which was used for manufacturing the particulate, water-insoluble medicine and complex according to the present invention.

FIG. 3 shows an apparatus 100 for forming ultrafine particles of a drug, which is usable in manufacturing the medicine of the present invention in a continuous manner.

As shown in FIG. 3, the supply part 20 is a vessel for storing a drug suspension which is water or a diluted alcohol having the drug mixed therein.

The supply part 20 has a predetermined volume. Further, the supply part 20 is preferably sealable so that the concentration of the supplied drug suspension does not change.

At a lower portion of the supply part 20, a conduit 30 is connected, and the supply part 20 communicates with the conduit 30. The drug suspension charged into the supply part 20 can be discharged to the conduit 30.

As shown in FIG. 3, the conduit 30 is provided with a pump 40. The pump 40 supplies the drug suspension to the microflow channel 60 described below. Herein, the term "microflow channel" means a flow channel which is formed by precise processing and which has a width of micron order. The pump 40 is capable of controlling the flow of the drug suspension to a desired flow rate. Especially when the drug suspension is continuously passed through the microflow channel 60, it is desirable that the pump 40 be capable of controlling the flow of the drug suspension to a constant flow rate. On the other hand, when the drug suspension is intermittently passed through the microflow channel 60, it is desirable that the pump 40 be capable of stopping or allowing the flow of the drug suspension at a desired timing. When the flow of the drug suspension is stopped, a laser beam generated from the light source 10 can be reliably irradiated onto the drug.

As shown in FIG. 3, the conduit 30 has connected thereto a microflow-channel introductory part 50, and communicates with the microflow-channel introductory part 50. By driving the pump 40, the drug suspension charged into the supply part 20 can be supplied to the microflow-channel introductory part 50 via the conduit 30.

The microflow-channel introductory part 50 has a substantially cuboid shape. The microflow-channel introductory part 50 temporarily stores the drug suspension supplied from the supply part 20, so as to render uniform the flow rate of the drug suspension flowing through the microflow channel 60 described below. The volume of the microflow-channel introductory part 50 can be appropriately selected, depending on the type of the drug suspension to be treated, and the flow rate generated by the pump 40.

In the example described above, the shape of the microflow-channel introductory part 50 is substantially cuboid. However, the shape of the microflow-channel introductory part 50 is not particularly limited, as long as the microflow-channel introductory part 50 is capable of rendering the flow rate of the drug suspension passing through the microflow channel 60 (described below) substantially uniform. For example, the microflow-channel introductory part 50 may be formed of a curved surface, such as a substantially cylindrical shape. The shape of the microflow-channel introductory part 50 can be appropriately selected depending on the flow rate of the drug suspension passing through the microflow channel 60, and the type and size of the drug within the suspension.

Figure 4:
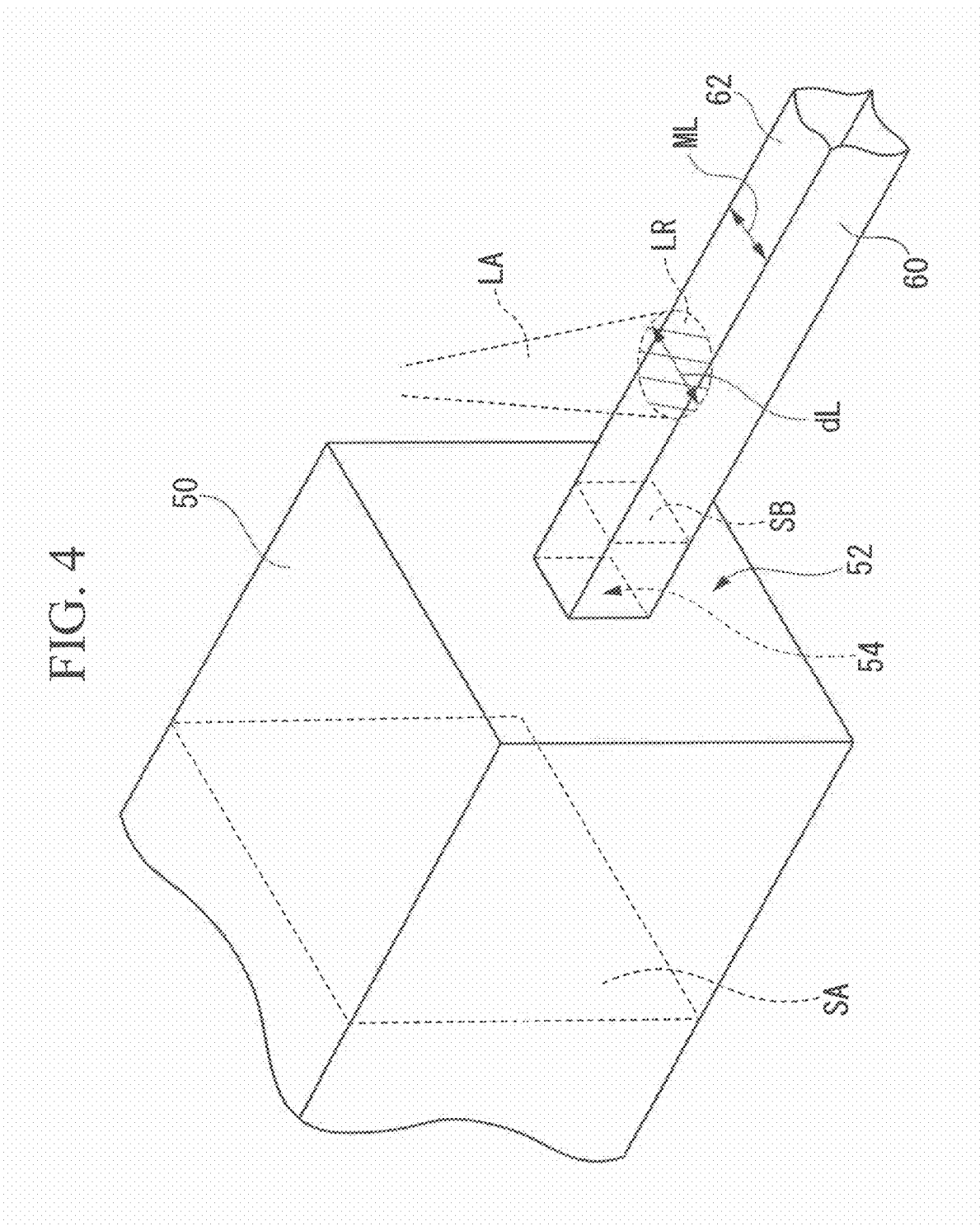
FIG. 4 is a schematic diagram showing an expanded, perspective view of the microflow-channel introductory part 50 and the microflow channel 60.

As shown in FIG. 4, the microflow-channel introductory part 50 has connected thereto the microflow channel 60, and communicates with the microflow channel 60. As shown in FIG. 4, the microflow-channel introductory part 50 has a discharge face 52. At substantially the center of the discharge face 52, an opening 54 is formed. The microflow channel 60 is connected to this opening 54. By this configuration, the drug suspension can be supplied from the microflow-channel introductory part 50 to the microflow channel 60 via the opening 54.

By irradiating the laser beam generated from the light source 10 onto the drug suspension passing through the microflow channel 60, ultrafine particles of the drug can be formed.

The microflow channel 60 has a long cuboid shape, and the cross-section taken along the plane perpendicular to the lengthwise direction of the microflow channel 60 is substantially square. It is preferable that the length ML of a side of this square (see FIG. 4) is 1.1 to 200 times the diameter of the drug, more advantageously 3 to 60 times. By setting the length ML of a side of the square within this range, the flow of the drug within the microflow channel 60 can be smoothed, so that clogging of the microflow channel 60 by the drug can be avoided, and the laser beam can be accurately irradiated onto the drug.

The shape of the microflow channel 60 is not particularly limited to cuboids, as long as the portion to be irradiated with the laser beam generated from the light source 10 (the portion located in the irradiation region LR described below) is even.

Further, in the example described above, the cross-section taken along the plane perpendicular to the lengthwise direction of the microflow channel 60 is substantially square. However, the cross-section may be a rectangle or the like, as long as the laser beam can be accurately irradiated onto the drug.

The microflow channel 60 is made of a transparent material such as a quartz glass, which is capable of transmitting the laser beam generated from the light source 10.

As shown in FIG. 4, the laser beam LA generated from the light source 10 is irradiated onto a portion of the upper face 62 of the microflow channel 60. The irradiation region LR of the laser beam LA (the region indicated with oblique lines in FIG. 4) is substantially circlular. By making the diameter dL of the irradiation region LR longer than the length ML of the shortwise direction of the upper face 62, the laser beam can be satisfactorily irradiated into the microflow channel 60.

By driving the above-mentioned pump 40, the drug suspension is allowed to flow into the microflow channel 60 from the microflow-channel introductory part 50, and the drug passes through the microflow channel 60. Drawing attention to a certain drug, the drug passes through the microflow channel 60 following the flow of the suspension to arrive at the irradiation region LR of the laser beam LA. The drug is present in the irradiation region LR for a while, and then, the drug comes out of the irradiation region LR.

When a pulsed laser beam is used and the drug is present in the irradiation region LR for a long time, the drug gets irradiated with a pulsed beam a plurality of times. As described above, when the drug is allowed to pass through the microflow channel 60, the irradiation period tL can be regarded as the period during which the drug is present in the irradiation region LR.

As described above, by irradiating the drug with the laser beam, ultrafine particles of the drug can be formed. The number of irradiations of the drug with a pulsed beam can be determined, so as to form ultrafine particles having a desired size. The number of irradiations with a pulsed beam can be changed by adjusting the above-mentioned pulse period T or the flow rate of the drug. Thus, in the irradiation region LR of the laser beam, the drug is irradiated with a pulsed beam at least once.

It is preferable that the cross-sectional area SA (see FIG. 4) of the microflow-channel introductory part 50 be two or more times of the cross-sectional area SB (see FIG. 4) taken along the plane perpendicular to the lengthwise direction of the microflow channel 60. In general, the flow rate VL of the drug passing through the microflow channel 60 tends to exhibit a distribution (hereafter, referred to as a "flow rate distribution") such that the flow becomes slowest near the walls of the microflow channel and fastest near the center line of the microflow channel (see FIG. 5B). When such a flow rate distribution is generated, the drug flowing near the walls of the microflow channel 60 exhibits a low flow rate, so that the period during which the drug is present in the irradiation region LR becomes long. On the other hand, in such a case, the drug flowing near the center line of the microflow channel 60 exhibits a high flow rate, so that the period during which the drug is present in the irradiation region LR becomes short. That is, when a pulsed laser beam is irradiated, the number of pulsed beam irradiations of the drug flowing near the walls of the microflow channel 60 becomes large, whereas the number of pulsed beam irradiations of the drug flowing near the center line of the microflow channel 60 becomes small. Thus, the amount of the size-reduction treatment of the drug varies depending on the position at which the drug flows. Therefore, it is possible that the size of the ultrafine particles of the drug becomes heterogeneous. By making the cross-sectional area SA of the microflow-channel introductory part 50 two times or more of the cross-sectional area SB of the microflow channel 60, the flow rate distribution of the drug can be rendered substantially uniform, so that heterogeneity in the size of the ultrafine particles of the drug can be prevented.

As described above, by driving the above-mentioned pump 40, the drug suspension is allowed to flow into the microflow channel 60 from the microflow-channel introductory part 50. The flow rate VL (see FIG. 5A) of the drug passing through the microflow channel 60 preferably satisfies the relation VL<K×dL/tL. Here, the flow rate VL is the flow rate of the drug which is in a state where the above-mentioned flow rate distribution is not observed, or in a state where the above-mentioned flow rate distribution can be disregarded. By setting the flow rate VL of the drug within the above-mentioned range, the drug can be irradiated with the laser beam without any excess or deficiency of irradiation, so that the drug can be reduced to a desired size. For example, when the drug is irradiated with a pulsed laser beam, the irradiation can be performed an appropriate number of times.

Here, dL represents the diameter of the laser beam upon irradiation (see FIG. 4), tL represents the above-mentioned irradiation period (see FIG. 2), and K represents a constant which can be determined within the range of 1 to 0.1, depending on the type of drug. K is not particularly limited to the above-mentioned range, and is preferably set such that the number of pulsed beam irradiations of the drug passing the irradiation region LR becomes sufficient for forming ultrafine particles of the drug. The thus formed ultrafine particles of the drug have a size of 50 to 200 nm.

Figure 5A:
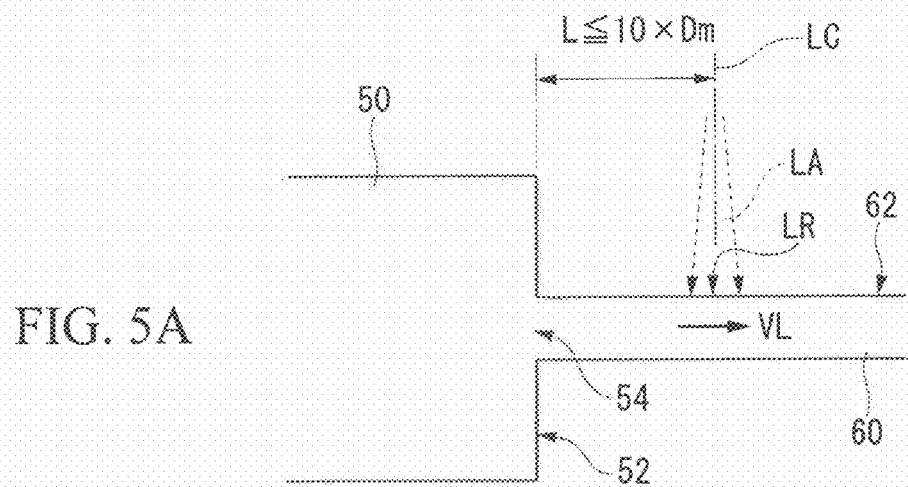
FIG. 5A is a cross-sectional view of the microflow-channel introductory part 50 and the microflow channel 60.
Figure 5B:
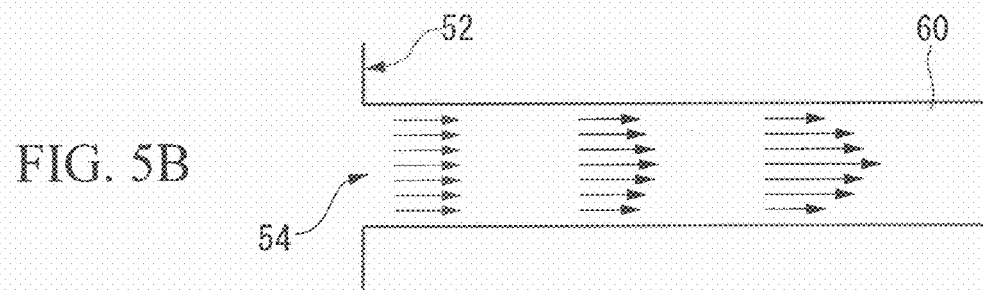
FIG. 5B is a cross-sectional view showing the flow rate distribution of the organic substance passing through the microflow channel 60.

FIG. 5A is a cross-sectional view of the microflow-channel introductory part 50 and the microflow channel 60. In the microflow channel 60, with respect to the portion to be irradiated with the laser beam LA, it is preferable that the distance from the discharge face 52 of the microflow-channel introductory part 50 to the center LC of the irradiation region LR of the laser beam LA be no more than 10×Dm (see FIG. 5A). Here, Dm is the hydraulic diameter of the microflow channel 60, and Dm is equal to 4×(cross-sectional area SB of the microflow channel 60)/(Perimeter of the cross-section of the microflow channel 60). For example, when the cross-section of the microflow channel 60 is a square having a length of ML on each side, Dm is calculated as follows:

$$Dm = 4 \times ML^2 / 4mL = ML$$

The above-mentioned flow rate distribution of the drug passing through the microflow channel 60 tends to increase as the drug flows away from the discharge face 52 of the microflow-channel introductory part 50. Therefore, by setting the portion to be irradiated with the laser LA within the above-mentioned range, the drug can be irradiated with the laser beam LA before the flow rate distribution of the drug passing through the microflow channel 60 becomes large. As a result, the ultrafine particles of the drug can be reliably formed, and the size of the ultrafine particles can be rendered substantially uniform.

Figure 5C:
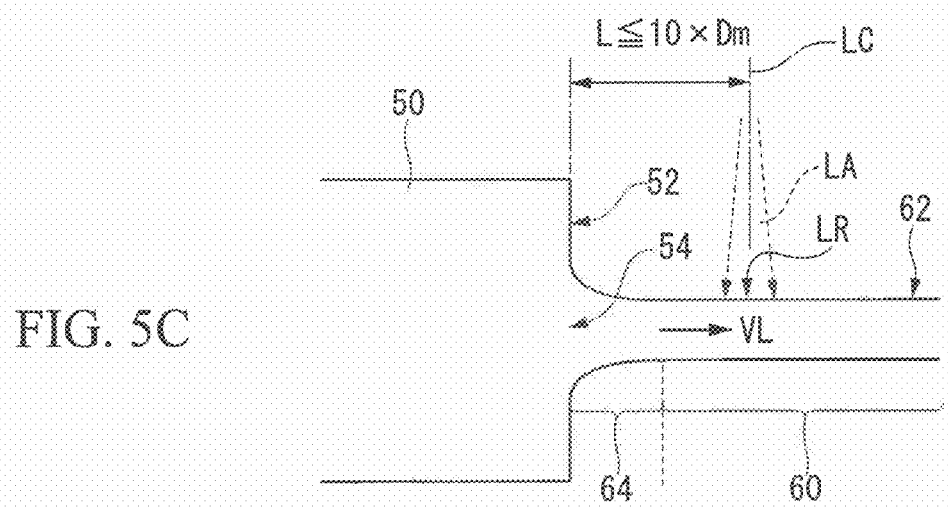
FIG. 5C is a cross-sectional view showing an embodiment in which a transition part 64 is provided between the microflow-channel introductory part 50 and the microflow channel 60.

In the example described above, the microflow channel 60 is directly connected to the opening 54 formed in the microflow-channel introductory part 50. However, as shown in FIG. 5C, a transition part 64 may be formed between the microflow-channel introductory part 50 and the microflow channel 60. The transition part 64 is formed in a manner such that the cross-section thereof becomes smaller as it becomes further from the opening 54 formed in the microflow-channel introductory part 50. The transition part 64 formed in this manner functions as an approach section, so as to render the flow rate of the drug flowing into the microflow channel 60 closer to being uniform. The shape of the transition part 64 can be appropriately selected depending on the flow rate and viscosity of the drug suspension.

As shown in FIG. 3, the microflow channel 60 has a collecting part 70 connected thereto, and communicates with the collecting part 70. The collecting part 70 is a vessel for storing the drug suspension which has been irradiated with the laser beam within the microflow channel 60.

It is preferable that the collecting part 70 be provided with an agglomeration prevention device 72. The agglomeration prevention device 72 includes a piezoelectric transducer which applies ultrasonic waves to the drug suspension stored in the collecting part 70. By the propagation of the ultrasonic waves to the drug suspension, the ultrafine particles of the drug can be prevented from agglomeration. The intensity and wavelength of the ultrasonic waves generated from the agglomeration prevention device 72 can be appropriately selected depending on the size of the ultrafine particles of the drug and the type of the drug. In the example described above, the agglomeration prevention device 72 generates ultrasonic waves to effect the prevention of agglomeration. However, any other agglomeration prevention device which is capable of preventing agglomeration of the ultrafine particles of the drug may be used.

In the vessel of the collecting part 70, a magnetic-drive impeller 74 may be provided. The magnetic-drive impeller 74 can be rotated by applying a magnetic field from the outside of the collecting part 70. By rotating the magnetic-drive impeller 74, the drug suspension stored within the collecting part 70 can be stirred, thereby preventing agglomeration of the ultrafine particles of the drug. The size and number of revolutions of the magnetic-drive impeller 74 can be appropriately selected depending on the size of the ultrafine particles of the drug and the type of the drug.

Subsequently, with respect to the ultrafine particles of the drug obtained in the manner as described above, the electric charge is measured. The electric charge is measured by a zeta potentiometer. The zeta potential may be positive or negative, depending in the core substance. The ultrafine particles are subjected to an electrostatic interaction or hydrophobic interaction with one or more polymer electrolytes having a charge opposite to the ultrafine particles to form a complex, thereby preventing agglomeration of the ultrafine particles.

Explanation is given below of a method and apparatus for producing such complex.

Figure 6:
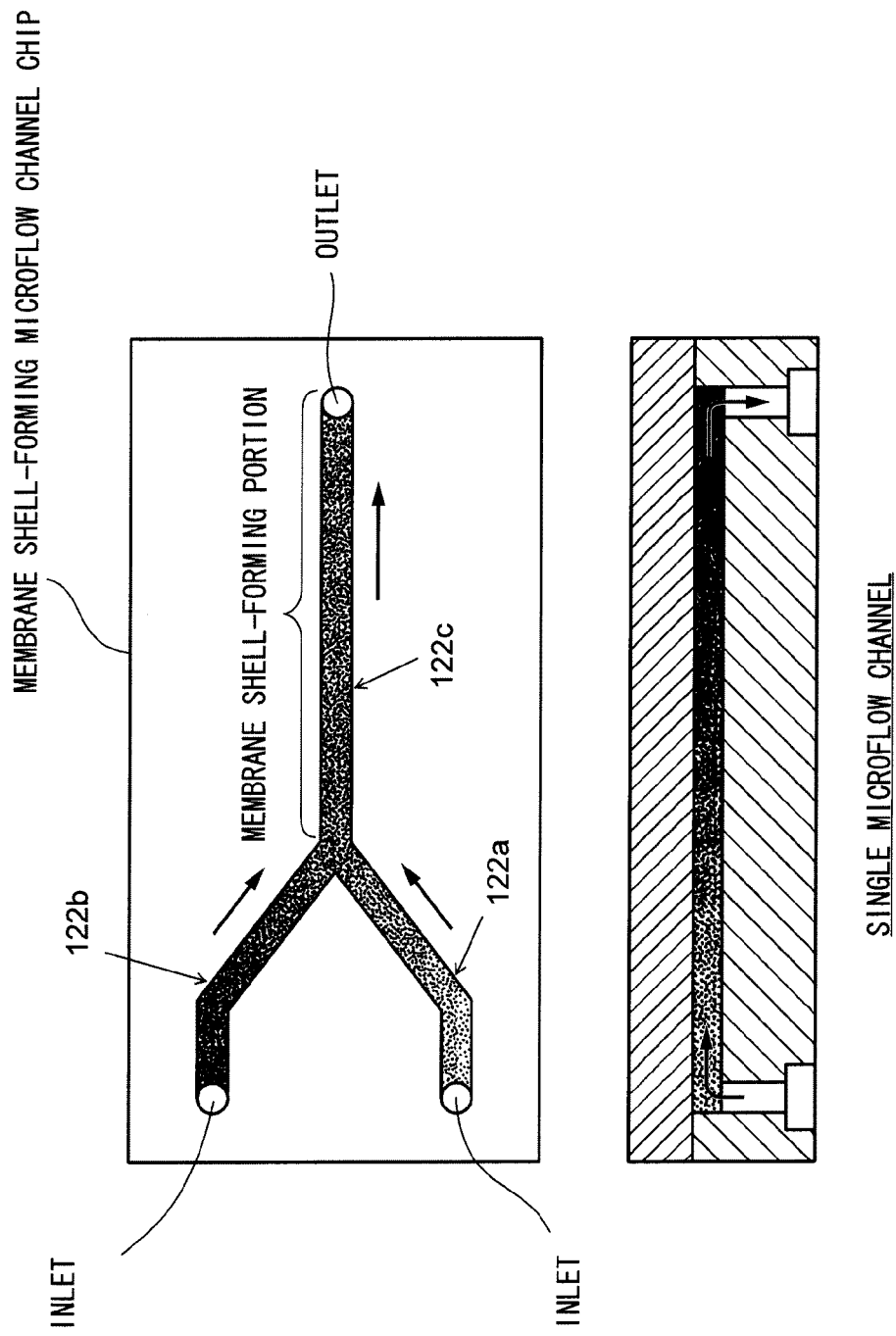
FIG. 6 is a diagram showing one embodiment of a coating part using a single microflow channel.
Figure 7:
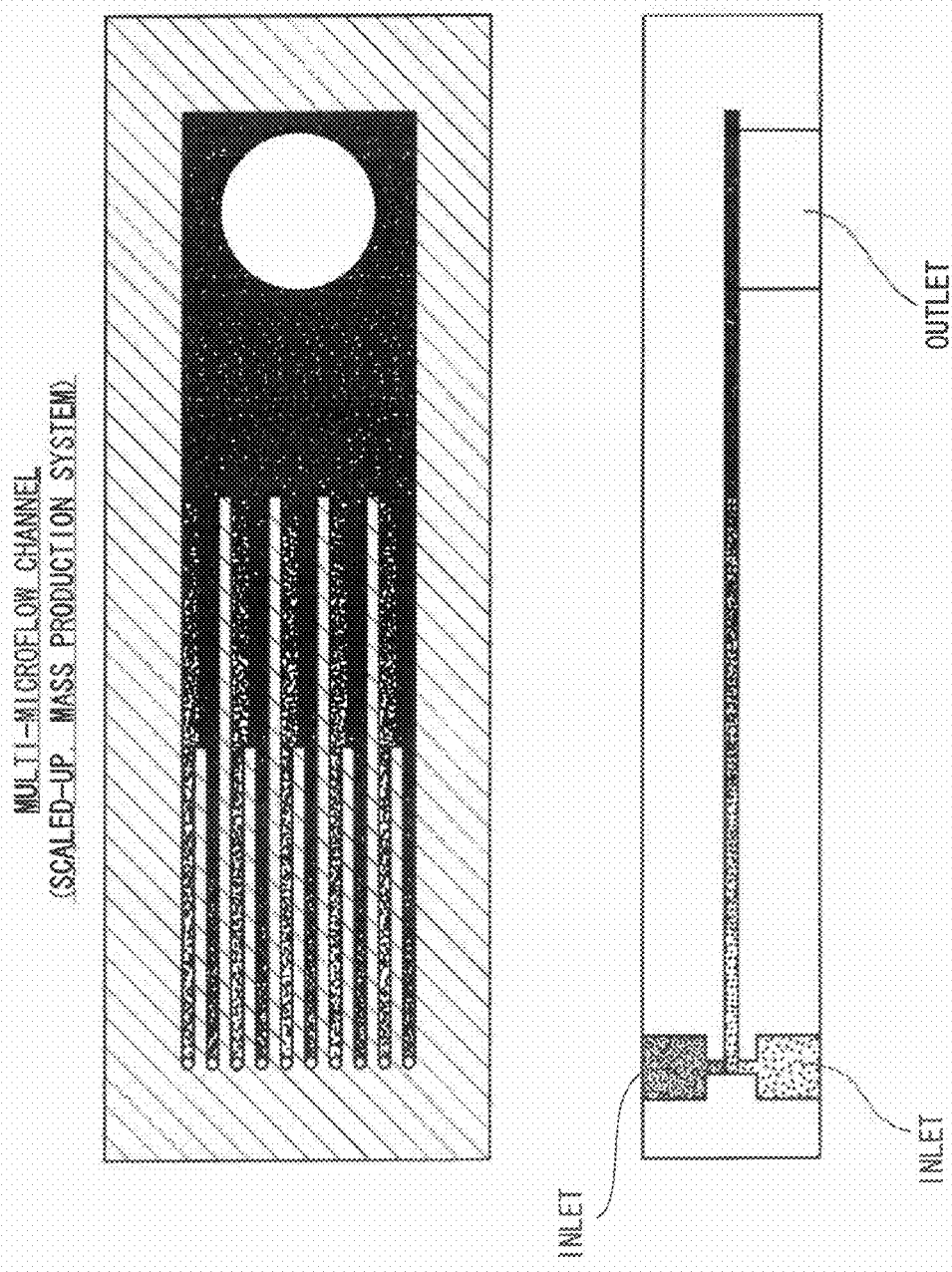
FIG. 7 is a diagram showing one embodiment of a coating part using a multi-microflow channel.

One embodiment of a polymer membrane shell-coating part in which the drug suspension and a polymer electrolyte solution are used to form a polymer electrolyte membrane shell on the outer surface of the ultrafine particles is explained, with reference to FIGS. 6 and 7. The polymer membrane shell-coating part is one of the main components of the apparatus for coating ultrafine particles used in the present invention.

In the present embodiment, coating is performed by merging the flow of the drug suspension with the flow of the polymer electrolyte solution. Further, in the present embodiment, both of the drug suspension and the polymer electrolyte solution are passed through a microflow channel. FIG. 6 shows an embodiment of a polymer membrane shell-coating part using a single microflow channel in which the drug suspension and the polymer electrolyte solution are respectively passed through microflow channels which merge together. FIG. 7 shows an embodiment of a polymer membrane shell-coating part using a multi-microflow channel which is provided with a plurality of single microflow channels shown in FIG. 6.

Firstly, an explanation is given below of the embodiment of a polymer membrane shell-coating part using a single microflow channel as shown in FIG. 6. A discharge microflow channel 76 is provided at a lower portion of the backside of the collecting part 70 shown in FIG. 3 (i.e., lower portion of the face opposite to the face where inlet from the microflow channel 60 is provided). Here, this microflow channel is effective in preventing the agglomeration of particles size-reduced by the apparatus for forming ultrafine particles. It is especially preferable to set the width of the microflow channel slightly larger than the maximum diameter of the ultrafine particles flowing within the suspension. However, in view of the fluctuation of particle diameter and precision in producing the microflow channel, the width of the microflow channel is preferably set in the range of 1.1 to 500 times, more preferably 50 to 500 times of the maximum diameter of the particles flowing.

Further, the microflow channel through which the polymer electrolyte solution is passed can be set at the same size as the above-mentioned microflow channel through which the ultrafine-particle suspension is passed. The polymer electrolyte solution passed through the microflow channel contains a polymer electrolyte having a charge opposite to that of the outermost layer of the ultrafine particles which are bonded to or coated with the polymer electrolyte. Namely, when the outermost layer of the ultrafine particles contained in the suspension has a negative charge, a cationic polymer electrolyte solution having a positive charge is passed through the microflow channel. Likewise, when the outermost layer of the ultrafine particles contained in the suspension has a positive charge, an anionic polymer electrolyte solution having a negative charge is passed through the microflow channel.

The angle at which the microflow channels merge can be selected from acute angles to obtuse angles. The angle at which the microflow channels merge is preferably from 0 to 180 degrees, more preferably from 0 to 5 degrees especially for a multi microflow channel.

As explained above, in each of the polymer membrane shell-coating parts, an ultrafine-particle suspension and a polymer electrolyte having a charge opposite to that of the outermost layer of the ultrafine particles are used. Therefore, the ultrafine particles and the polymer electrolyte are attracted to each other by electrostatic force by simply merging the flow of the suspension and the flow of the polymer electrolyte solution, so that strong membrane shells can be easily formed.

Although an example using a single microflow channel is illustrated in FIG. 6, a multi microflow channel may be used to perform the coating of the polymer membrane shell in the same manner as mentioned above, thereby enabling a production of complex with high productivity.

Figure 8:
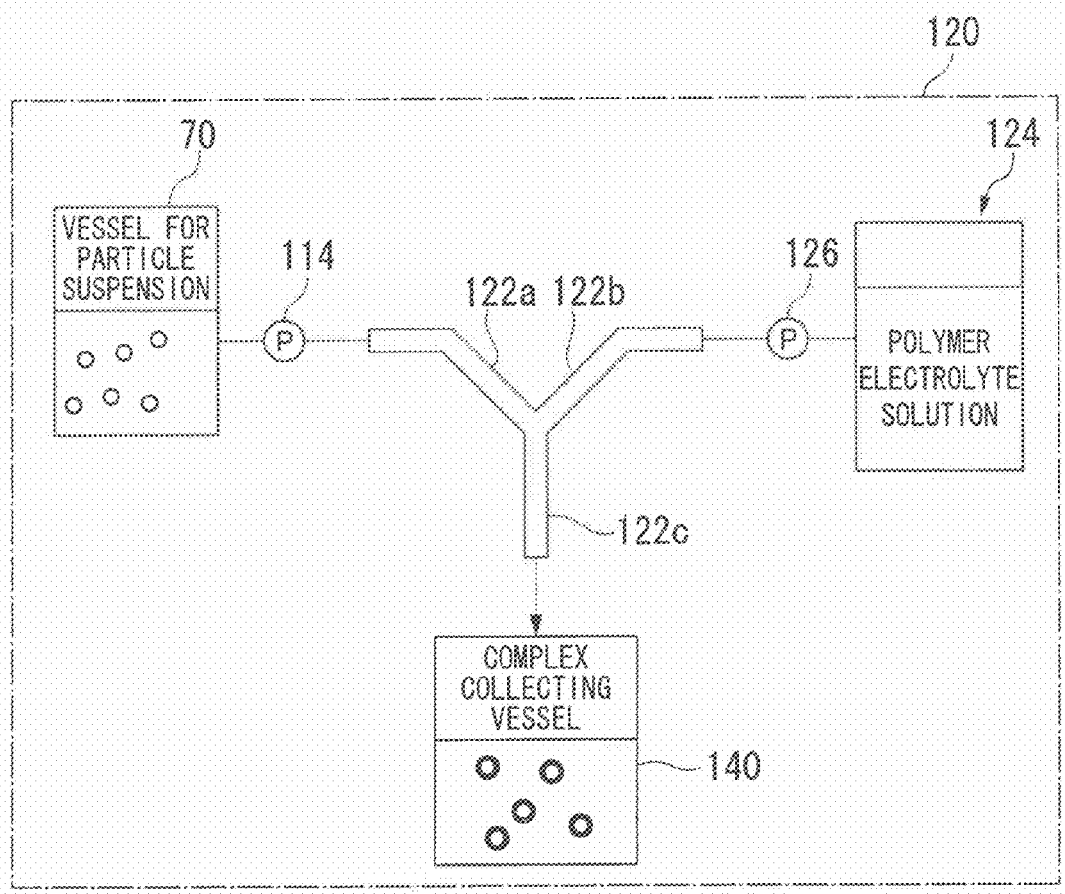
FIG. 8 is a line diagram showing a general view of one embodiment of the apparatus and method for coating particles used in the present invention, following the flow of the ultrafine-particle suspension and the polymer electrolyte solution.

Next, a general explanation is given of the apparatus and method for sequentially producing complex from the ultrafine-particle suspension contained in the collecting part 70, with reference to the line diagram shown in FIG. 8.

The apparatus used in the present invention for coating ultrafine particles is mainly composed of a polymer membrane-shell coating part 120. Further, the polymer membrane-shell coating part 120 is mainly composed of: an ultrafine-particle suspension vessel 70 (the above-mentioned collecting part 70) for containing a suspension of ultrafine particles prior to coating; a microflow channel 122a for ultrafine-particle suspension; a microflow channel 122b for polymer electrolyte solution; a merged microflow channel 122c which is formed by merging of the microflow channel 122a with the microflow channel 122b; a tank 124 for polymer electrolyte solution, where a polymer electrolyte solution is stored; a complex collecting vessel 140 for collecting the polymer membrane shell-coated ultrafine particles following coating treatment (i.e., complex formed); pumps; conduits; and valves.

For the sake of simplifying the figure, the microflow channel used in the polymer membrane shell-coating part 120 is shown in the form of single microflow channel. However, in practice, a multi-microflow channel having the required number of microflow channels corresponding to the production rate of ultrafine particles can be used.

Next, an explanation is given following the flow of the ultrafine-particle suspension. The ultrafine-particle suspension is stored in the particle suspension vessel 70. Taking example of a case where water is used as a solvent, ultrafine particles are suspended in water, and the outer surfaces of the ultrafine particles are ionized in water to exhibit a positive or negative charge. For sake of simplicity, explanation is given of a case where the outer surfaces of the ultrafine particles have a negative charge. In this case, a cationic polymer electrolyte solution is used as the polymer electrolyte.

In this state, using a pump 114, the suspension of the ultrafine particles prior to coating is transferred from the ultrafine-particle suspension vessel 70 to the microflow channel 122a for ultrafine-particle suspension provided within the polymer membrane shell-coating part 120. Likewise, using a pump 126, the cationic polymer electrolyte solution stored in a tank 124 for polymer electrolyte solution is transferred to the microflow channel 122b for polymer electrolyte solution.

Then, the microflow channel 122a for ultrafine-particle suspension and the microflow channel 122b for polymer electrolyte solution merge together to form a merged microflow channel 122c. In the merged microflow channel 122c, the ultrafine-particle suspension and the cationic polymer electrolyte solution are mixed together, whereby the outer surfaces of the ultrafine particles contact the cationic polymer electrolyte to form cationic membrane shells, thereby obtaining complexes having cationic membrane shells.

Finally, a cationic mixture of the ultrafine-particle suspension and the cationic polymer electrolyte solution containing the complexes formed is transferred to the complex collecting vessel 140.

In the case where the outer surfaces of the ultrafine particles have a positive charge, complexes can be formed in substantially the same manner as described above, except that an anionic polymer electrolyte solution is used as the polymer electrolyte.

Hereinbelow, the present invention will be described in more detail with reference to the Examples.

EXAMPLES

Example 1

(1) Conditions for Laser Irradiation

Using $Nd^{3+}$:YAG laser (Continuum, Surelite), a laser beam was generated by an Optical Parametric Oscillator (OPO) system (Continuum, SureliteOPO). The intensity of the laser beam was adjusted using an attenuation plate and an attenuator. The area of beam irradiation was estimated by irradiating a laser beam to a photosensitive paper provided at the front face of the quartz cell.

Laser:
Repetition frequency: 10 Hz
Pulse width: 7 ns
Excitation wavelength: 355 nm
Irradiation area: 0.28 $cm^2$
Size-reduction of ellipticine:
Intensity of laser beam: 100 $mJ/cm^2$
Total irradiation time: 10 seconds (2) Ellipticine Sample As a test sample, ellipticine (Fluka, >99%) was used, which was roughly pulverized to about 1 μm. As a solvent, a deionized water was used.

In the formation of ultrafine particles, 75 ml of a suspension of the test sample which had been irradiated with ultrasonic waves (SHARP, UT-205, high frequency: maximum of 200 W) was used. 3 ml of this test particle suspension was measured and charged into a quartz cell (1×1×5 $cm^3$) having an optical path length of 1 cm, and the quartz cell was irradiated with a laser beam while stirring with a magnetic stirrer.

The ultrafine particles formed were immediately coated with a polymer electrolyte added in advance for the purpose of stabilizing the ultrafine particles and preventing the ultrafine particles from agglomerating. Therefore, the laser beam was irradiated onto (a) a sample having a polymer electrolyte added thereto and (b) a sample having no polymer electrolyte added thereto, and a comparison was made between sample (a) and sample (b).

(a) Ellipticine+polymer electrolyte+aqueous dispersion

Polymer electrolyte: protamine (concentration: $1 \times 10^{-2}$ g/ml)

Ellipticine $4.1 \times 10^{-3}$ M (1.0 $mgml^{-1}$) as an anti-cancer drug was dispersed in water while irradiating with a laser beam. The resulting suspension was allowed to stand for 1 hour, and then the supernatant formed was evaluated.

Separately from the above, ellipticine $4.1 \times 10^{-3}$ M (1.0 $mgml^{-1}$) was dispersed in water without irradiating a laser beam. The supernatant of the resulting suspension was used as a control.

The concentration of the supernatant was estimated from the absorbance.

(b) Ellipticine+Aqueous Dispersion

Ellipticine $1.5 \times 10^{-4}$ M ($3.6 \times 10^{-2}$ $gl^{-1}$) was dispersed in water while irradiating a laser beam. The supernatant following the irradiation was evaluated.

Separately from the above, ellipticine $1.5 \times 10^{-4}$ M ($3.6 \times 10^{-2}$ $gl^{-1}$) was dispersed in water without irradiating a laser beam. The supernatant of the resulting suspension was used as a control.

The concentration of the supernatant was estimated from the absorbance.

As a result, it was found that the concentration of the supernatant of the suspension following irradiation of the laser beam in the presence of the polymer electrolyte was more than 100 times the supernatant of the suspension in the absence of the polymer electrolyte.

Concentration of the supernatant of the suspension following irradiation of laser beam in the presence of the polymer electrolyte: $>1.8 \times 10^{-5}$ g/ml.

(3) Evaluation of Ultrafine Particles (3-1) Evaluation of the purity of the ultrafine particles formed was performed in the following manner.

From the suspension following irradiation, the supernatant was taken out, and the solvent was vaporized by using a vacuum pump. Then, ethanol was added to the residue, and the resultant was analyzed by ultraviolet and visible ray spectroscopy (SHIMADZU, UV-3100. HITACHI, F-4500) and liquid chromatography (SHIMADZU,SPD-10).

Figure 9:
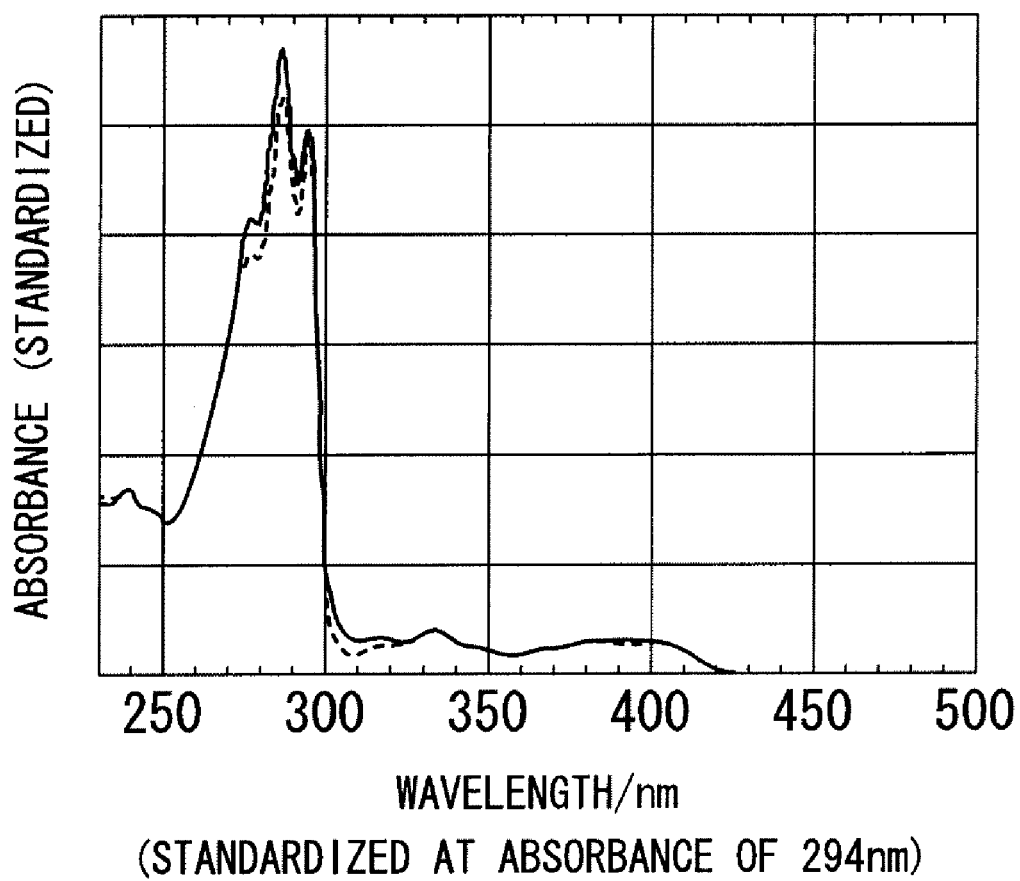
FIG. 9 is a diagram showing a comparison of absorption spectra of ethanol solutions prior to and following irradiation.

FIG. 9 shows a comparison of absorption spectra—ethanol solution prior to and following irradiation—. In FIG. 9, absorption spectrum (solid line) of unirradiated ellipticine ethanol solution and absorption spectrum (dotted line) of the ethanol solution following irradiation (100 $mJ/cm^2$, 10 seconds) are shown. From FIG. 9, almost no difference is observed between the absorption spectrum (solid line) of unirradiated ellipticine ethanol solution and the absorption spectrum (dotted line) of the ethanol solution following irradiation. From this result, it is understood that the ultrafine particles of ellipticine formed by laser beam irradiation are hardly decomposed.

Figure 10:
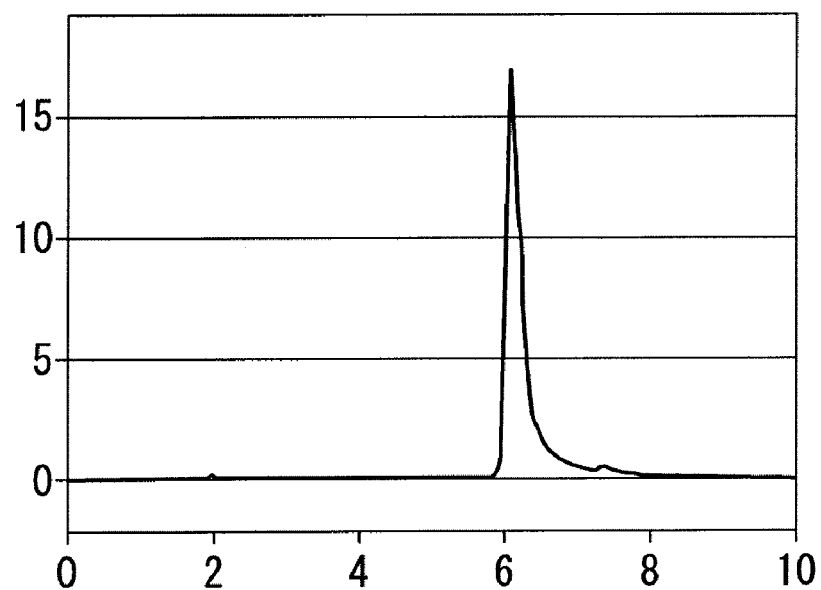
FIG. 10 is a liquid chromatogram of an ethanol solution of ellipticine following irradiation with a laser beam.

FIG. 10 is a chromatogram of the ethanol solution of ellipticine following laser beam irradiation. From FIG. 10, it is also understood that the ultrafine particles of ellipticine formed by laser beam irradiation are hardly decomposed.

Figure 11:
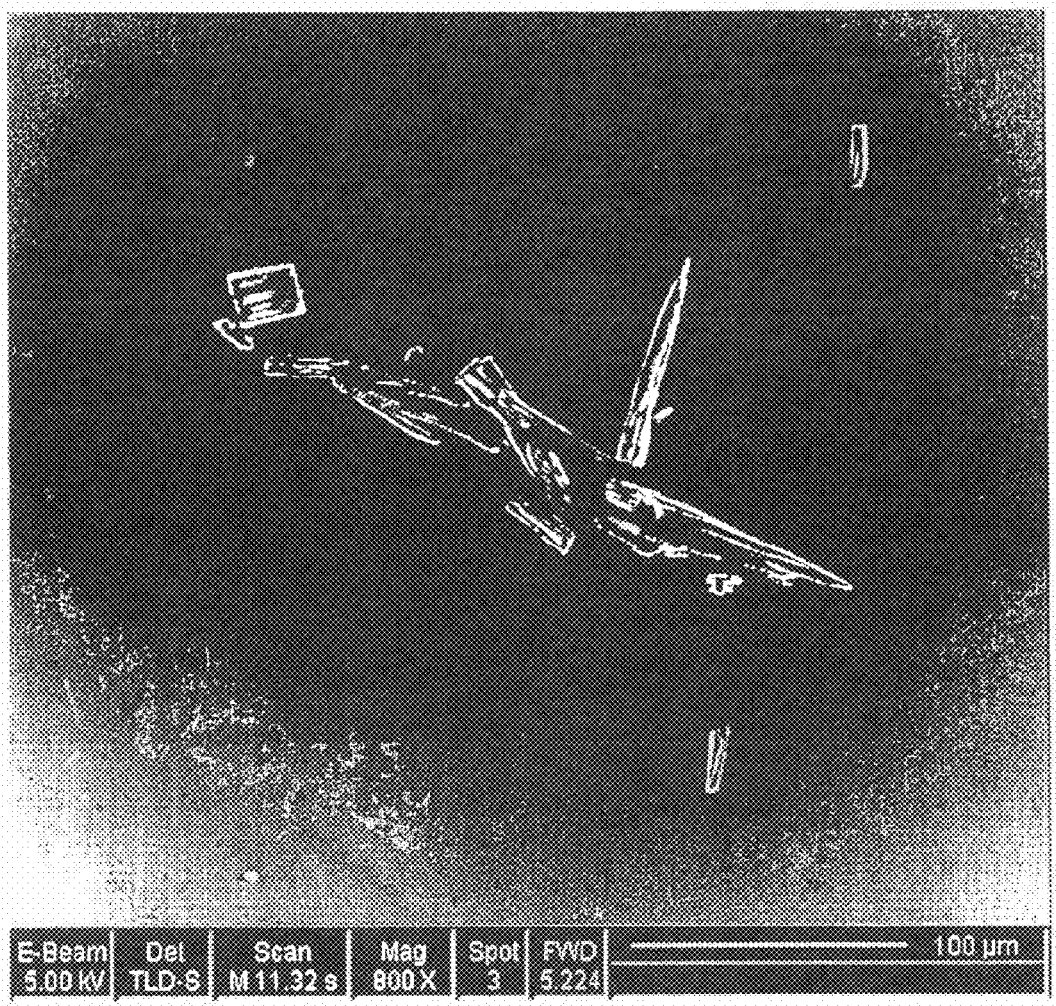
FIG. 11 is a SEM image of ellipticine prior to size-reduction.
Figure 12:
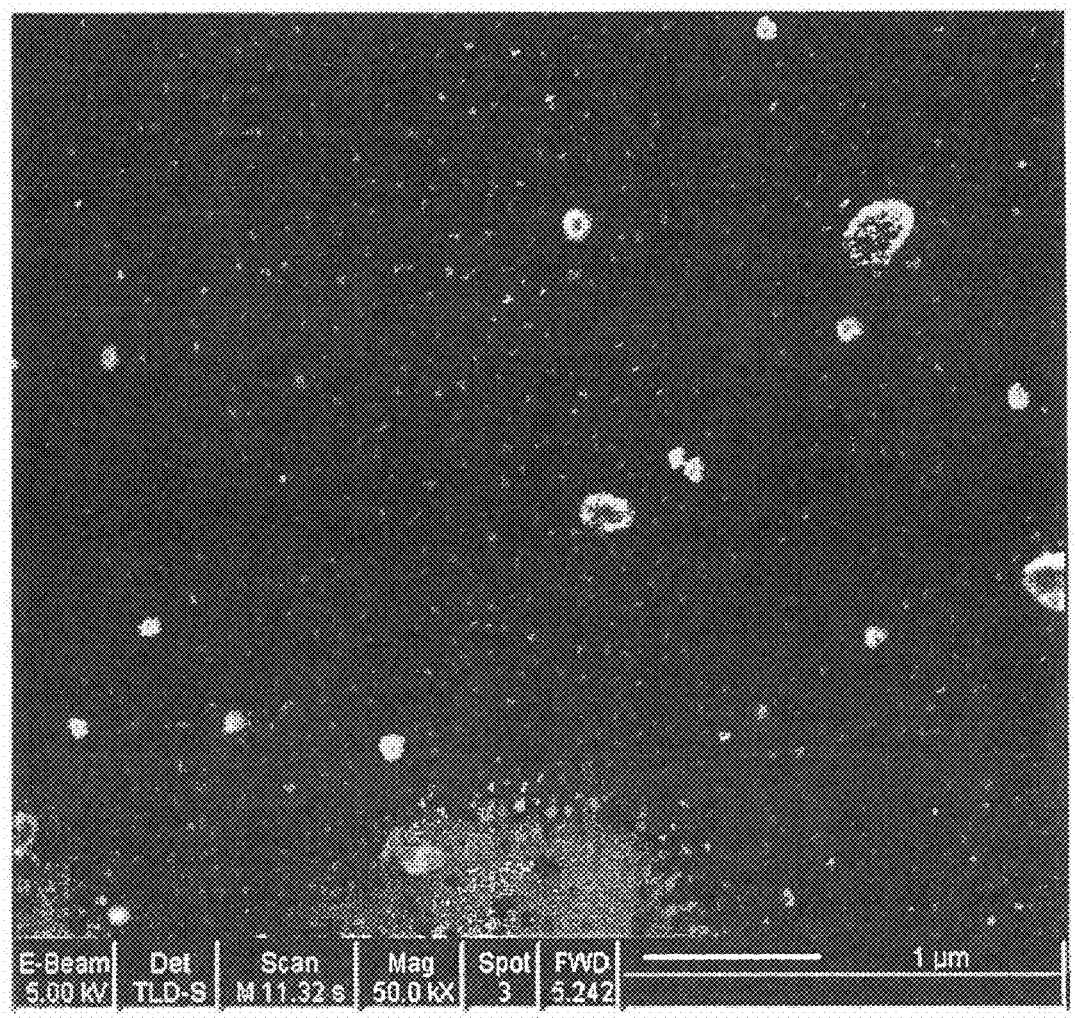
FIG. 12 is a SEM image of ultrafine particles of ellipticine.

(3-2) FIG. 11 is a SEM image of ellipticine prior to size-reduction treatment, and FIG. 12 is a SEM image of ultrafine particles of ellipticine (ellipticine following size-reduction treatment). The average diameter of the particles prior to the size-reducing treatment is about 1 μm, which is the limit size achieved by size-reduction using machines.

Observation was performed by FEI, Strata DB235-51. See attached microphotographs.

Figure 13:
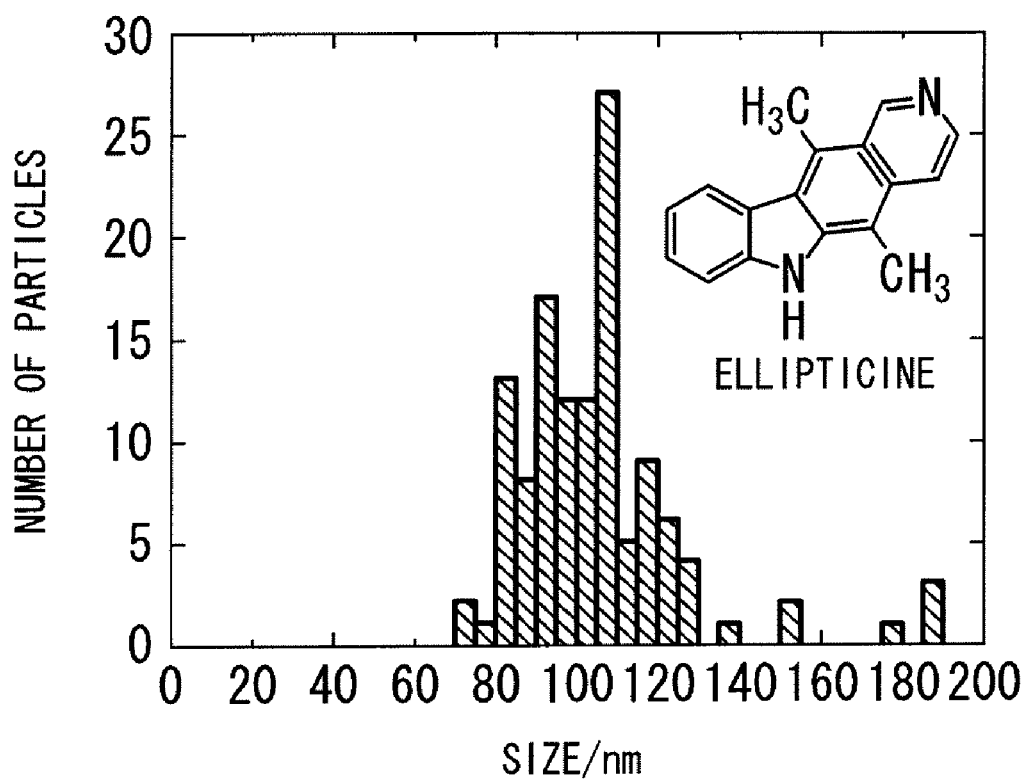
FIG. 13 is a histogram of particle diameter distribution of ultrafine particles of ellipticine.

(3-3) FIG. 13 is a histogram of the particle diameter distribution of the ultrafine particles of ellipticine.

From FIG. 13, almost all of the complexes of the present invention have a particle size distribution within the range of 70 to 130 nm, which meant that the particle size was uniform. The average diameter was 100 nm. The average diameter was determined by measuring the diameter of each particle using a microscope provided with a scale, and dividing the sum of the particle diameters by the number of particles.

Observation was performed by FEI, Strata DB235-51. Measurement was performed by MALVERN zeta sizer Nano-ZS.

In the present example, the thickness of the coating was 3 to 4 nm. Therefore, the thickness of the coating could be disregarded from the entire particle size.

(3-4) Cytotoxicity Test

Ellipticine which had been size-reduced by laser beam irradiation (concentration: 2 µg/ml) was diluted with the below-mentioned culturing solution, and test samples having concentrations of 1 µg/ml, 0.5 µg/ml, 0.25 µg/ml and 0.125 µg/ml were prepared. MCF-7 (MEM-culture medium) and L-1210 (RPMI-1640 culture medium) tumor cells were used as target cells. The cytotoxicity was evaluated by counting the number of viable cells following 24 hours of culturing, using Cell Counting Kit-8. More specifically, WST-8 (U.S. Pat. No. 2,757,348) as an indicate for dehydrogenase activities was used, and the color at 450 nm was evaluated.

$$Viability(\%) = (A_{samples} - A_{blank})/(A_{no-samples} - A_{blank})\ 100\%$$

wherein A is the absorbance at a wavelength of 450 nm exhibiting UV properties, $A_{samples}$ is the absorbance as measured when a sample was present, $A_{no-samples}$ is the absorbance as measured when a sample was not present but the polymer electrolyte was present, and $A_{blank}$ is the absorbance as measured when only the culture medium was present.

The 50% inhibiting activities on the cells were as follows.
MCF-7 cells: 0.21 mg/ml
L-1210 cells: 0.09 µg/ml The control could not be evaluated because ellipticine is insoluble in water. The values indicated in prior art documents cannot be directly compared with the present invention because an organic solvent such as DMSO is used.

From the results shown above, it has been proved that the ultrafine particles of an anti-cancer drug according to the present invention and a complex of the same with a polymer electrolyte exhibits an inhibiting activity to tumor cells, and that the ultrafine particles of an anti-cancer drug and the complex have a drug effect.

Example 2

Figure 14A:
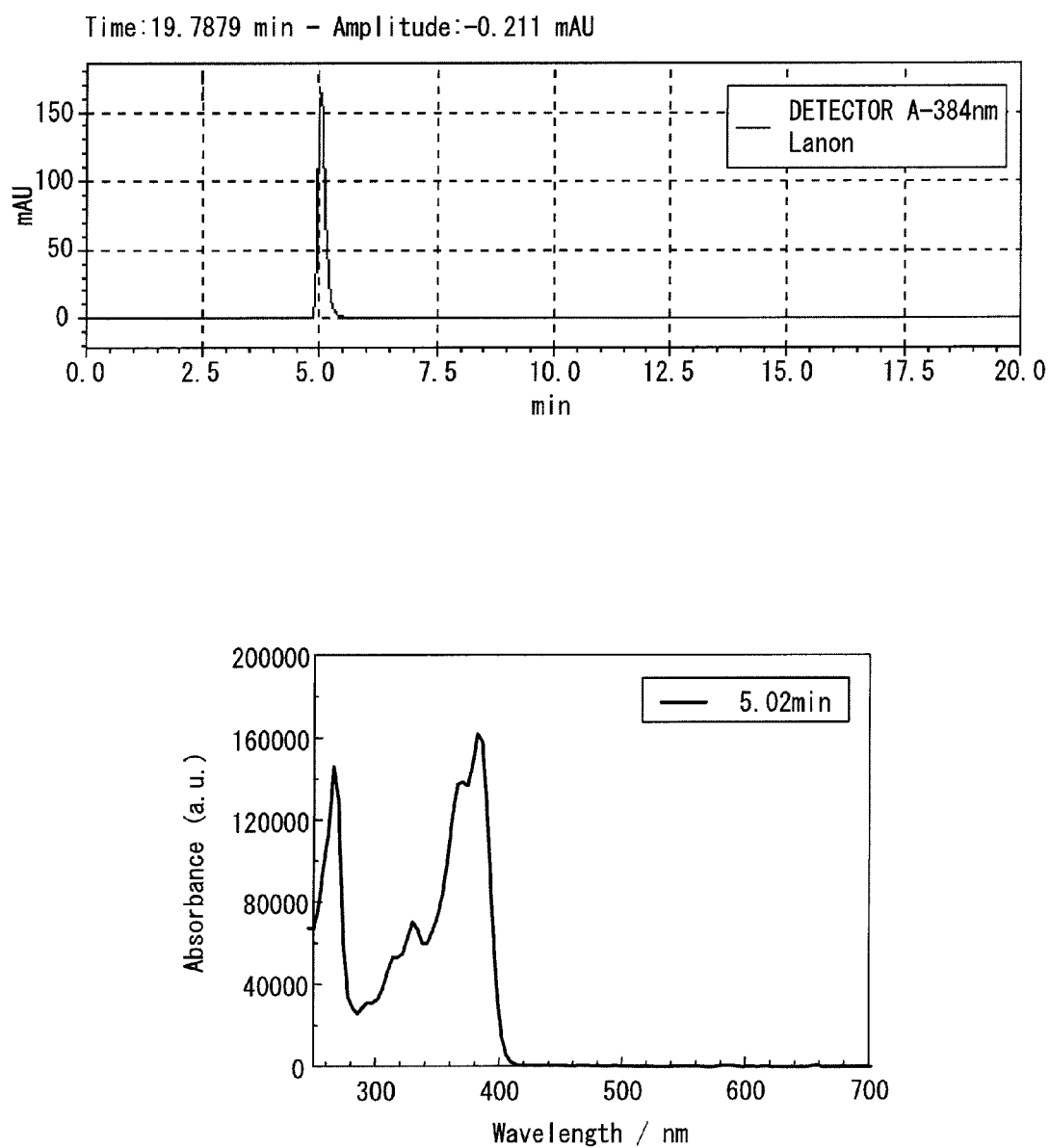
FIG. 14A is a chromatogram of SN-38 prior to laser irradiation (spreading solvent: ethanol) and results of HPLC analysis.

Preparation of SN-38 Nano Particles 0.01N HCl was diluted by 100 folds to obtain an aqueous solution of hydrochloric acid exhibiting a pH value of 4.0. To 20 ml of this solution was added 60 mg of SN-38 and the resultant was subjected to an ultrasonic treatment for 2 or more hours, to thereby obtain a suspension. Then, 2.0 ml of the suspension was measured out while stirring the suspension with a magnetic stirrer, and charged into a quartz cell having an optical path length of 1 cm. Then, 1 ml of the aqueous solution of hydrochloric acid exhibiting a pH value of 4.0 was further charged into the quartz cell, thereby obtaining a suspension having an SN-38 concentration of 2 mg/ml. Subsequently, the suspension was irradiated with a laser beam (420 nm excitation, 80 mJ/cm², 100 minutes) while thoroughly stirring with a magnetic stirrer. After the irradiation, the suspension was allowed to stand for 1 day at room temperature, and the supernatant of the resulting suspension was taken out and analyzed by absorbance spectroscopy, HPLC, and measurement of particle size distribution and SEM. As a result, it was found that nanosizing had proceeded without chemical decomposition of SN-38 caused by the laser beam irradiation under the above-mentioned conditions (see FIGS. 14A, 14B and FIG. 15). The yield of the nano particles formed was 50% or more, and the concentration was 1 mg/ml.

Figure 16:
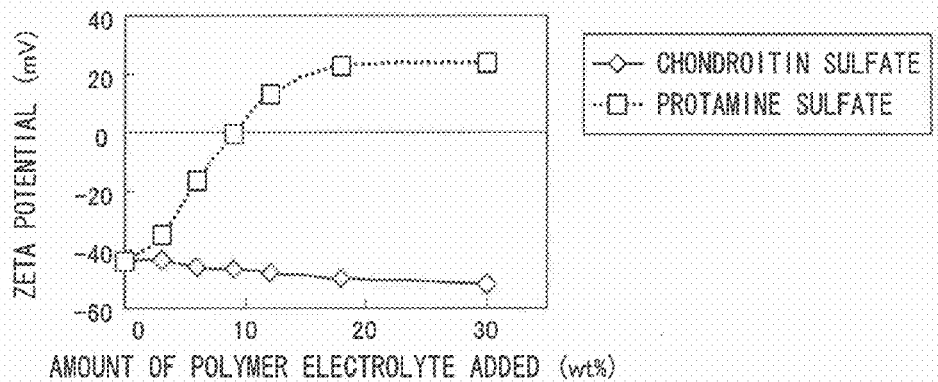
FIG. 16 is a graph showing changes in zeta potential by addition of a polymer electrolyte to SN-38 nano particles.

Preparation of SN-38 Nano Particles-Protamine Sulfate and SN-38 Nano Particles-Chondroitin Sulfate For the purpose of stabilizing the SN-38 nano particles (preventing self-agglomeration of SN-38 nano particles), protamine sulfate and chondroitin sulfate were respectively added to two separate samples of the above-mentioned supernatant having a concentration of 1 mg/ml, in an amount sufficient for rendering the zeta potential of the surface of the nanoparticles a predetermined value (more specifically, 10 mg/ml protamine sulfate (pH4) and 10 mg/ml chondroitin sulfate (pH4) were respectively added to two separate 1 mg/ml suspensions of SN-38 ultrafine particles in an amount of 30 wt %, based on the weight of the suspension of SN-38 ultrafine particles), so as to adjust the zeta potential to +19.9 mV and -47.2 mV, respectively (see FIG. 16).

Cytotoxicity Test of SN-38 Nano Particles

The cytotoxicity of the SN-38 nano particles was evaluated by counting the number of viable cells following 24 hours of culturing in the same manner as in the cytotoxicity test of ellipticine as described in item (3-4) of Example 1. The 50% inhibiting activity for MCF-7 cells was 100 nM. The DMSO solution and water suspension of SN-38 which were not irradiated with a laser beam and which were used as controls each exhibited a 50% inhibiting activity of 500 nM and 2,000 nM.

From the results above, it was shown that the nano-sized sample exhibited high ability of intracellular transport, as compared to the control.

Comparison of Anti-Tumor Effect of SN-38 Nano Particles, SN-38 nano Particles-Protamine Sulfate, SN-38 Nano Particles-Chondroitin Sulfate and Irinotecan Hydrochloride (CPT-11) using Nude Mice-Transplanted Human Tumor Test Laboratory Name: EXPERIMENTAL CANCER CHEMOTHERAPY RESEARCH LAB., Co., LTD.

Address: Halcushima3-13-1 Minou-shi Osaka-fu Japan

Materials and Method

1. Test Substances
   SN-38 nano particles
   SN-38 nano particles-protamine sulfate
   SN-38 nano particles-chondroitin sulfate
   Preservation conditions: The test substances were placed in an air-tightly sealed vessel and shielded, and preserved at room temperature (23° C.)
   Control drug: irinotecan hydrochloride (CPT-11)
2. Human Cancer Strain Used
   Gastric cancer H-23, 323th passage moderately differentiated-type adenocarcinoma
3. Test Animal
   BALB/cAJcl-nu nude mouse (male, Clea Japan Inc.)
4. Transplantation Method
   A nude mouse having tumor cells transplanted was killed by cervical dislocation, and the subcutaneously passage-cultured tumor cells were extracted. From the extracted tumor cells, the capsule and necrotic portion were removed, and the resultant was washed with RPMI medium. Thereafter, substantially uniform cubes having sides of 2 to 3 mm were cut out as tumor specimens, and the tumor specimens were transplanted subcutaneously onto the backs of 6-week-old mice using a trocar (transplantation day: Day 0).
5. Experiment Method
   Using vernier calipers, the maximum diameter (L), the transverse diameter (W) crossing the maximum diameter (L), and the thickness (D) were measured to the 0.5 mm scale. When the estimated volume of the tumor as determined by the formula: $V = \frac{1}{2} \times L \times W \times D$ became about 70 mm³ (7 days after transplantation), a control group and treatment group were set as 5 mice per each group, and the average values of the estimated tumor volumes and the standard deviations of the respective groups were set to be substantially equal. Then, administration to each of the groups was started.

The experiment was completed after 4 weeks from the starting day of administration. The tumor cell diameter was measured twice a week, and the weight was measured at the time of administration, so as to monitor the state of tumor cell proliferation and effect of drug administration, as well as any other physical changes. The mice were kept in a small vinyl isolator throughout the experiment, except for when they were moved to a clean bench through a sleeve to perform tumor cell transplantation, administration or weight measurement.

6. Dose and Administration Schedule
(1) Control (No drug treatment)
(2) CPT-11 60 mg/kg (i.v.) q4d×4 4 times in total
(3) SN-38 nano particles 10 mg/kg (i.v.) q4d×4 4 times in total
(4) SN-38 nano particles-protamine3 mg/kg (i.v.) q4d×4 4 times in total
(5) SN-38 nano particles-chondroitin sulfate 10 mg/kg (i.v.) q4d×4 4 times in total 7. Preparation of Sample Solution Each of SN-38 nano particles (1 mg/ml), stock solution of SN-38 nano particles-chondroitin sulfate (1 mg/ml) (for 10 mg/kg treatment group) and SN-38 nano particles-protamine sulfate (1 mg/ml) were respectively diluted with distilled water for injection to obtain 0.3 mg/ml sample solutions (for 3 mg/kg treatment group). Further, just before administration, 27% NaCl solution was added with a volume ratio of 1:30. CPT-11 was diluted with physiological saline to a concentration of 3 mg/ml.

8. Administration Method of Sample Solution

To each of the SN-38 nano particles, SN-38 nano particles-protamine and SN-38 nano particles-chondroitin sulfate treatment groups, the sample solution was administered within 25 minutes from the addition of NaCl. The sample solution was intravenously administered once a day in an amount of 0.1 ml per 10 g of the mouse weight, and the administration was performed once every 4 days and 4 times in total (q4d×4).

With respect to the CPT-11 treatment group, 3 mg/ml sample solution was intravenously administered twice a day (60 mg/kg treatment group), in an amount of 0.1 ml per 10 g of the mouse weight, and the administration was performed once every 4 days and 4 times in total (q4d×4). Further, with respect to the control group, no drug administration was performed.

9. Evaluation of Drug Effect

On the final day of the experiment, tumor cells were extracted from the control group (C) and the treatment group (T). From the average weight of the tumor cells, the tumor-proliferation inhibiting efficiency (IR) was determined by the formula shown below. IR of below 58% was evaluated as "non-effective", IR≧58% was evaluated as "effective", and IR≧80% was evaluated as "significantly effective".

$$IR=(1-T/C)\times 100(\%)$$

The statistical significance between the weights of tumor cells of each group was determined by Student's T test (two-tailed).

Further, the average estimated tumor volumes of the control group (C) and the treatment group (T) were measured sequentially during the experiment, and the tumor volume IR was determined in the similar manner as mentioned above, to thereby determine the maximum proliferation inhibiting efficiency (max. IR) during the experiment. Furthermore, when the average estimate tumor volume at the end of the experiment was larger than that at the time of administration, it was evaluated as having size-reducing effect.

The influence of the drug on the host was evaluated by considering the change in weight and expression of symptoms.

Results

A study was made by comparing the tumor proliferation inhibiting effect of each of SN-38 nano particles, SN-38 nano particles-protamine sulfate and SN-38 nano particles-chondroitin sulfate with that of CPT-11, using 323th passage of nude-mouse transplanted human gastric cancer H-23 (moderately differentiated-type adenocarcinoma).

1. Tumor Proliferation Inhibiting Effect
1) CPT-11 60 mg/kg Treatment Group

As the number of times performing the administration increased, the tumor volume IR increased. 2 days after the 4th administration (d21), the maximum tumor proliferation inhibiting efficiency (max. IR) during the experiment became 69.1%, and hence, a drug effect was confirmed. However, thereafter, the tumor volume IR gradually decreased, and the tumor volume IR on the final day of the experiment (d35) was 22.4%, and hence, the drug effect was evaluated as non-effective. With respect to the tumor weight, no statistical significance against the control group was observed by the t-test.

2) SN-38 Nano Particles 10 mg/kg Treatment Group 4 days after the first administration (d11), the tumor volume IR became 57.7% which was the maximum value during the treatment. 3 days after the second administration (d14), tendency of tumor-cell size-reduction was exclusively observed among all treatment groups. As a result, the tumor volume IR was found to be 59.9%, and drug effect was exclusively confirmed among all treatment groups only after the second administration. 3 days after the third administration (d18), the tumor volume IR became higher as 73.4%. 2 days after the fourth administration (d21), the max. IR of 74.7% was observed, and the tumor proliferation inhibiting effect was significant. 9 days after the fourth administration (d28), the tumor volume IR was 61.1%, and drug effect was exclusively confirmed among all treatment groups. However, the drug effect gradually decreased, and the tumor weight IR on the final day of the experiment (d35) was 45.9%, and hence, the drug effect was evaluated as non-effective. Nevertheless, by the t-test regarding the tumor weight, statistical significance of p<1% against the control group was observed, which was p<5% higher than the CPT-11 60 mg/kg treatment group.

3) SN-38 Nano Particles-Protamine Sulfate 3 mg/kg Treatment Group 3 days after the third administration (d18), the tumor volume IR was 57.5%, and hence, a tumor proliferation inhibiting effect slightly higher than the CPT-11 60 mg/kg treatment group was observed.

2 days after the fourth administration (d21), the max. IR of 62.1% was observed, and hence, a drug effect was confirmed. Thereafter, the tumor volume IR gradually decreased. On the final day of the experiment (d35), the tumor weight IR was 38.9%, and hence, the drug effect was evaluated as non-effective. Nevertheless, by the t-test regarding the tumor weight, statistical significance of p<1% against the control group was observed. Further, the IR was advantageous over the CPT-11 60 mg/kg treatment group.

4) SN-38 Nano Particles-Chondroitin Sulfate 10 mg/kg Treatment Group 3 days after the third administration (d18), the tumor volume IR was 65.3%, and hence, a drug effect was confirmed. Specifically, the second high tumor proliferation inhibiting effect following the tumor proliferation inhibiting effect of the SN-38 10 mg/kg treatment group was confirmed. 2 days after the fourth administration (d21), the max. IR of 65.4% was observed. However, thereafter, the IR rapidly decreased. On the final day of the experiment (d35), the tumor weight IR was 28.5%, and hence, the drug effect was evaluated as non-effective. Nevertheless, by the t-test regarding the tumor weight, statistical significance of p<5% against the control group was observed.

Conclusion

The SN-38 nano particles 10 mg/kg treatment group exhibited an apparently high tumor proliferation inhibiting effect as compared to the CPT-11 treatment group. Further, the CPT-11 treatment group exhibited marked lowering of the tumor proliferation inhibiting effect by stopping administration. On the other hand, although the SN-38 nano particles 10 mg/kg treatment group exhibited lowering of the tumor proliferation inhibiting effect by stopping administration, the degree of lowering was much smaller than the CPT-11 treatment group. Furthermore, in the SN-38 nano particles 10 mg/kg treatment group, no weight reduction was observed, and no serious side-effect was observed.

Figure 17:
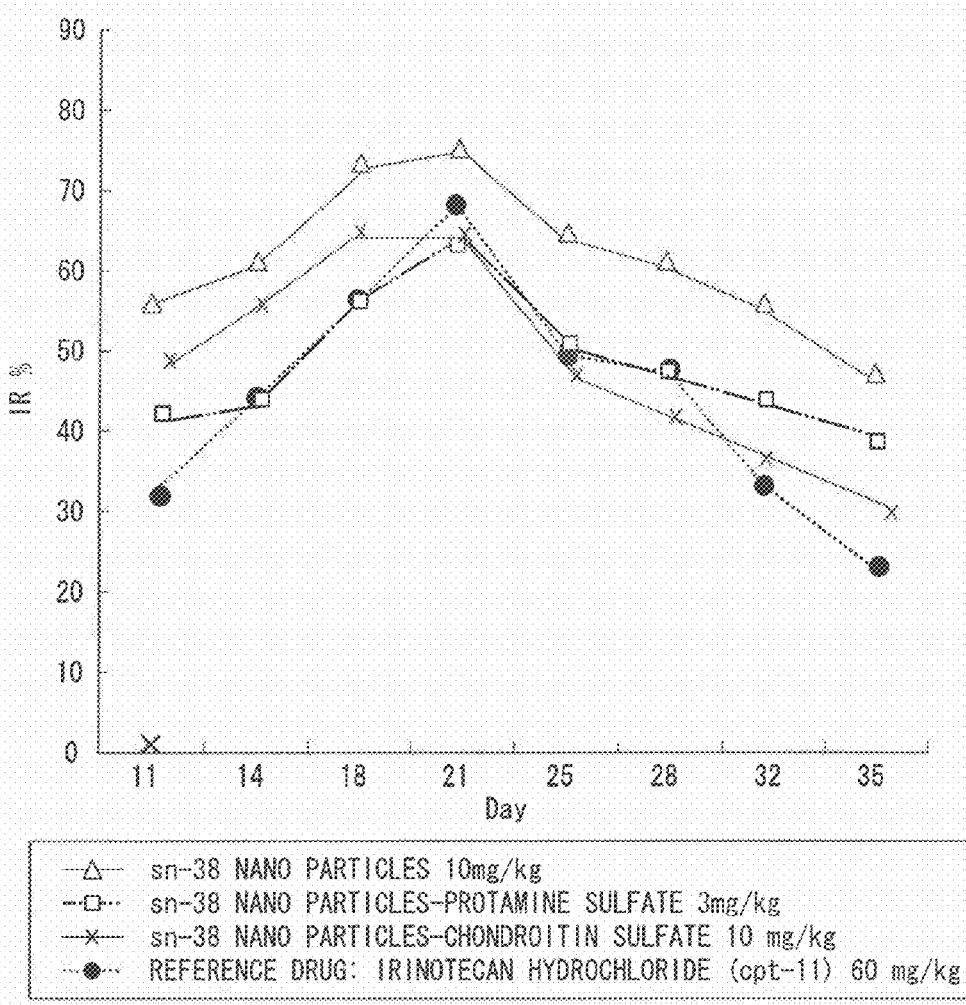
FIG. 17 is a graph showing the anti-tumor effects of SN-38 nano particles, SN-38 nano particles-protamine sulfate, SN-38 nano particles-chondroitin sulfate and irinotecan hydrochloride (CPT-11), using human tumor tissue transplanted into nude mice.

The SN-38 nano particles-protamine sulfate 3 mg/kg treatment group and the SN-38 nano particles-chondroitin sulfate 10 mg/kg treatment group both exhibited a high tumor proliferation inhibiting effect, as compared to the CPT-11 treatment group. Especially up to 3 days after the third administration (d18) and between d32 to d35 (final day of the experiment), the tumor proliferation inhibiting effect was advantageous over the CPT-11 treatment group (see FIG. 17).

Example 3

Preparation of 10-Hydroxy-Camptothecin Nano Particles

A suspension of 10-hydroxy-camptothecin with a concentration of 0.5 mg/ml was prepared in the same manner as in the preparation of SN-38 nano particles.

Figure 18B:
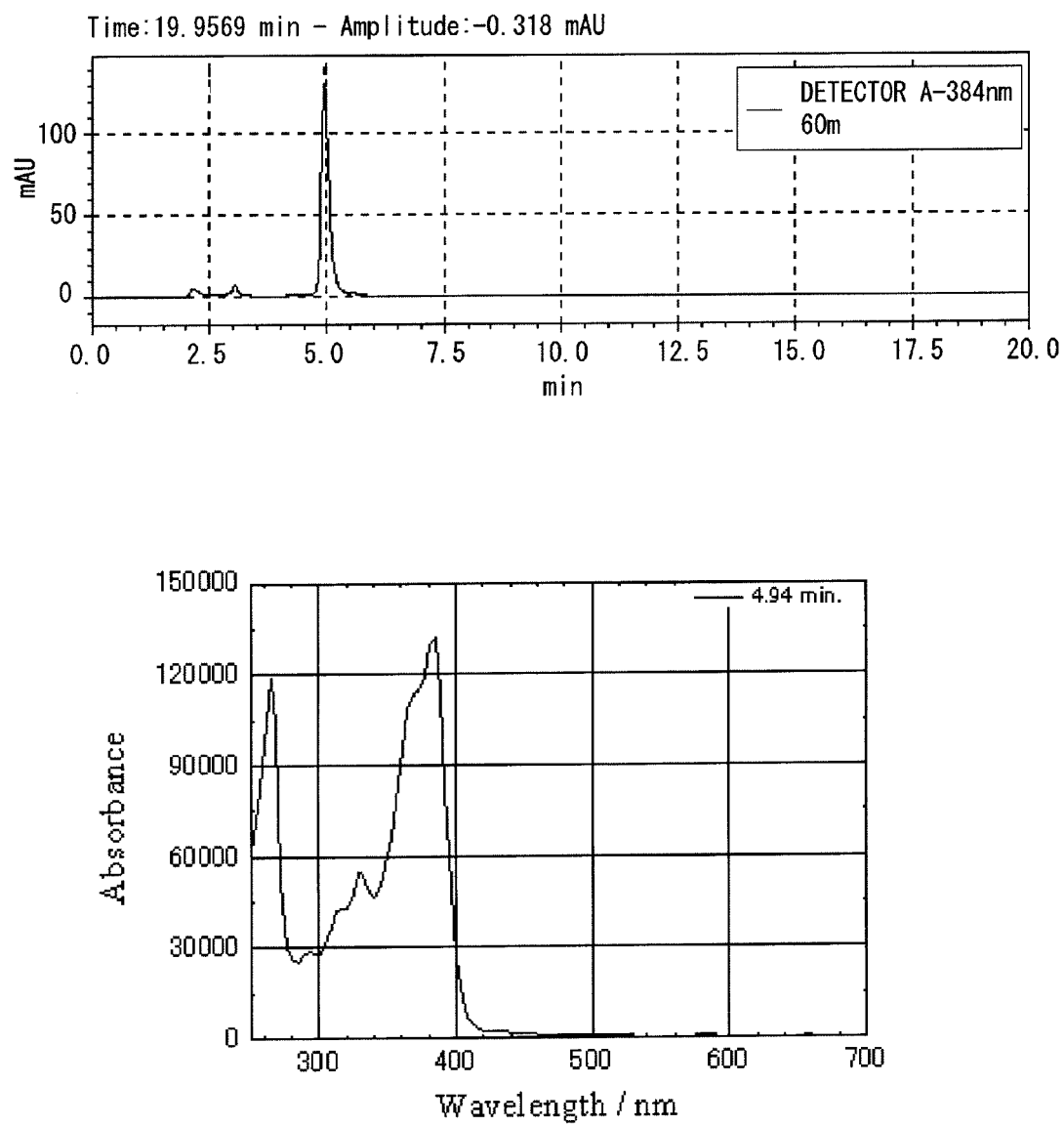
FIG. 18B shows a chromatogram of supernatant of 10-hydroxy-camptothecin suspension following laser irradiation (spreading solvent: ethanol) and results of HPLC analysis.

Subsequently, the suspension was irradiated with a laser beam (430 nm excitation, 40 mJ/cm$^2$, 60 minutes) while thoroughly stirring with a magnetic stirrer. After the irradiation, the suspension was subjected to centrifugal separation, and the supernatant of the resulting suspension was taken out and analyzed by absorbance spectroscopy, HPLC, and measurement of particle size distribution and SEM (see FIGS. 18A, 18B and 19). As a result, it was found that the yield of the nano particles formed was 50% or more, and the concentration was 0.25 mg/ml.

Cytotoxicity Test of 10-Hydroxy-Camptothecin Nano Particles

The cytotoxicity of the 10-hydroxy-camptothecin nano particles was evaluated by counting the number of viable cells following 72 hours of culturing in the same manner as in the cytotoxicity test of ellipticine as described in item (3-4) of Example 1. The 50% inhibiting activity for MCF-7 cells was 100 nM. The DMSO solution and water suspension of 10-hydroxy-camptothecin which were unirradiated with a laser beam and which were used as controls each exhibited a 50% inhibiting activity of 100 nM and 500 nM.

From the results above, it was shown that the nano-sized sample exhibited high ability of intracellular transport, as compared to the control.

Comparison of Anti-Tumor Effect of 10-Hydroxy-Camptothecin Nano Particles and Irinotecan Hydrochloride (CPT-11) using Nude Mice-Transplanted Human Tumor Test Laboratory
Name: EXPERIMENTAL CANCER CHEMOTHERAPY RESEARCH LAB., Co., LTD.
Address: Hakushima3-13-1 Minou-shi Osaka-fu Japan
Materials and Method
1. Test Substances
10-hydroxy-camptothecin nano particles
Control drug: irinotecan hydrochloride (CPT-11)
2. Human Cancer Strain Used
Gastric cancer H-23, moderately differentiated-type adenocarcinoma
3. Test Animal
BALB/cAJcl-nu nude mouse (male, Clea Japan Inc.)
4. Transplantation Method A nude mouse having tumor cells transplanted was killed by cervical dislocation, and the subcutaneously passage-cultured tumor cells were extracted. From the extracted tumor cells, the capsule and necrotic portion were removed, and the resultant was washed with RPMI medium. Thereafter, substantially uniform cubes having sides of 2 to 3 mm were cut out as tumor specimens, and the tumor specimens were transplanted subcutaneously onto the backs of 5-week-old mice using a trocar (transplantation day: Day 0).

5. Experiment Method

Using vernier calipers, the maximum diameter (L), the transverse diameter (W) crossing the maximum diameter (L), and the thickness (D) were measured to the 0.5 mm scale. When the estimated volume of the tumor as determined by the formula: $V=\frac{1}{2}\times L\times W\times D$ became about 100 mm$^3$ (7 days after transplantation), a control group and treatment group were set as 5 mice per each group, and the average values of the estimated tumor volumes and the standard deviations of the respective groups were set to be substantially equal. Then, administration to each of the groups was started.

The experiment was ended after 4 weeks from the starting day of administration. The tumor cell diameter was measured twice a week, and the weight was measured at the time of administration, so as to monitor the state of tumor cell proliferation and effect of drug administration, as well as any other physical changes. The mice were kept in a small vinyl isolator throughout the experiment, except for when they were moved to a clean bench through a sleeve to perform tumor cell transplantation, administration or weight measurement.

6. Dose and Administration Schedule
(1) Control: physiological saline 0.1 ml/10 g of mouse weight (i.v.) d7, d11, d14 3 times in total
(2) CPT-11 60 mg/kg (i.v.) d7, d11, d14 3 times in total
(3) 10-hydroxy-camptothecin nano particles 5 mg/kg (i.v.) d7, d8, d11, d12, d14, d15 6 times in total
(4) 10-hydroxy-camptothecin nano particles 2.5 mg/kg (i.v.) d7, d8, d11, d12, d14, d15 6 times in total 7. Preparation of Sample Solution 1.8% NaCl solution was added to 10-hydroxy-camptothecin nano particle solution (0.25 mg/ml) to obtain a 0.125 mg/ml sample solution. CPT-11 was diluted with physiological saline to a concentration of 3 mg/ml.

8. Administration Method of Sample Solution

To each of the 10-hydroxy-camptothecin nano particle treatment groups, the 0.125 mg/ml sample solution was administered within 25 minutes from the preparation thereof. Specifically, the sample solution was intravenously administered to the 5 mg/kg treatment group twice a day in an amount of 0.2 ml per 10 g of the mouse weight, and once a day in an amount of 0.2 ml per 10 g of the mouse weight to the 2.5 mg/kg treatment group. The administration was performed 6 times in total on d7, d8, d11, d12, d14, d15.

With respect to the CPT-11 treatment group, 3 mg/ml sample solution was intravenously administered twice a day (60 mg/kg treatment group), in an amount of 0.1 ml per 10 g of the mouse weight. The administration was performed 3 times in total on d7, d11 and d14. Further, with respect to the control group, physiological saline was administered 3 times in the same manner as in the CPT-11 treatment group.

9. Evaluation of Drug Effect

On the final day of the experiment, tumor cells were extracted from the control group (C) and the treatment group (T). From the average weight of the tumor cells, the tumor-proliferation inhibiting efficiency (IR) was determined by the formula shown below. IR of below 58% was evaluated as "non-effective", IR≧58% was evaluated as "effective", and IR≧80% was evaluated as "significantly effective".

$$IR = (1 - T/C) \times 100(\%)$$

The statistical significance between the weights of tumor cells of each groups was determined by Student's T test (two-tailed).

Further, the average estimated tumor volumes of the control group (C) and the treatment group (T) were measured sequentially measured during the experiment, and the tumor volume IR was determined in the similar manner as mentioned above, to thereby determine the maximum proliferation inhibiting efficiency (max. IR) during the experiment. Furthermore, when the average estimate tumor volume at the end of the experiment was larger than that at the time of administration, it was evaluated as having size-reduction effect.

The influence of the drug on the host was evaluated by considering the change in weight and the expression of symptoms.

Results

A study was made by comparing the tumor proliferation inhibiting effect of 10-hydroxy-camptothecin nano particles with that of CPT-11, using 317th passage of nude-mouse transplanted human gastric cancer H-23 (moderately differentiated-type adenocarcinoma).

1. Tumor Proliferation Inhibiting Effect

1) CPT-11 60 mg/kg Treatment Group

Significant tumor proliferation inhibiting effect was observed from the start of administration. At the time of the third administration (d14), the tumor volume IR was 60.7%, and hence, drug effect was confirmed. Further, 4 days after the third administration (d18), the max. IR became 69.0%. By the t-test regarding the tumor weight, statistical significance of p<1% against the control group was observed. However, thereafter, the proliferation rate of tumor cells increased, and the IR after 3 days (d21) became 50.7%, and hence, the drug effect was evaluated as non-effective. The proliferation rate increased even more, and the tumor volume IR after 18 days from the start of administration (d25) became lower than the CPT-11 30 mg/kg treatment group in which proliferation had reached a peak. As a result, the surfaces of the tumor cells were ulcerated. The tumor volume IR on the finish day of the experiment (d35) was 14.1%. The tumor weight IR was 14.1%, and hence, the drug effect was evaluated as non-effective. Further, no statistical significance against the control group was observed by the t-test regarding the tumor weight.

2) 10-Hydroxy-Camptothecin Nano Particles 5 mg/kg Treatment Group

From the start of administration, size-reduction of tumor cells was observed, and the tumor volume IR on the third administration day (d11) was 63.2%, and hence, drug effect was exclusively observed among all treatment groups. Thereafter, proliferation gradually started again, but a significant inhibiting effect was observed as compared to the control group, and the tumor volume IR was enhanced. 3 days after the sixth administration (d18), the tumor volume IR was 85.4% (max. IR), and hence, a significant drug effect was observed. By the t-test regarding the tumor volume, statistical significance of p<1% against the control group was observed. However, thereafter, the proliferation rate increased and the tumor volume IR gradually decreased. Nevertheless, the tumor volume IR after 10 days from the end of the sixth administration (d25) was 62.3%, and hence, drug effect was exclusively observed among all treatment groups. Thereafter, the proliferation of the control group reached a peak, and hence, the tumor proliferation rate of the 10-hydroxy-camptothecin nano particles treatment groups markedly increased, and the tumor volume 1R rapidly decreased. The tumor volume IR on the final day of the experiment (d35) was 23.1%. The tumor weight IR was 19.4%, and hence, the drug effect was evaluated as non-effective. Further, no statistical significance against the control group was observed by the t-test regarding the tumor weight.

3) 10-Hydroxy-Camptothecin Nano Particles 2.5 mg/kg Treatment Group

From the start of administration, the proliferation rate of tumor cells was moderate, and a significant proliferation inhibiting effect was observed. 2 days after the fourth administration (d14), the tumor volume IR was 68.0%, and hence, drug effect was confirmed. 3 days after the sixth administration (d18), the max. IR of 76.4% was observed. By the t-test regarding the tumor volume, statistical significance of p<1% against the control group was observed. The tumor volume IR after further 3 days (d21) was 68.0%, and hence, drug effect was confirmed. During the last stage of the experiment, the number of animals having the surface of the tumor cells ulcerated increased. Therefore, the proliferation of tumor cells reached a peak, and the tumor volume IR became higher than the 5 mg/kg treatment group. The tumor volume IR on the final day of the experiment (d35) was 28.7%. The tumor weight IR was 25.5%, and hence, the drug effect was evaluated as non-effective, but the tumor weight IR was highest of all treatment groups. However, no statistical significance against the control group was observed by the t-test regarding the tumor weight.

2. Side-Effects

With respect to the maximum weight loss (max. wt. loss) of the treatment groups, CPT-11 60 mg/kg treatment group was 0.4% which was very small, and no weight loss was observed in the 10-hydroxy-camptothecin nano particles 2.5 mg/kg treatment group from the first day of the experiment.

In the 10-hydroxy-camptothecin nano particles 5 mg/kg treatment group, a moderate max. wt. loss of 9.1% was observed 3 days after the sixth administration (d15), and soft stool was confirmed with respect to one mouse (No. 5) among the 5 mice of the group. However, after further 3 days (d21), the weight loss recovered, and the weight continued to recover up to the final day of the experiment. No other significant side-effects were observed. In the control group, although the average weight loss was small at the start of the experiment, tendency of weight loss was observed at the last stage of the experiment, despite the fact that the weight of proliferated tumor cells was included. Especially, 1 mouse (No. 2) among the 5 mice of the group suffered marked weight loss, and was the only mouse among the 30 mice (i.e., all of the treated mice) to have a weight lower than that at the start of the experiment, as measured on the final day of the experiment. The body state of the control group and the CPT-11 60 mg/kg treatment group was not good.

3. Comparison of 10-Hydroxy-Camptothecin Nano Particles and CPT-11

From a comparison of the CPT-11 60 mg/kg treatment group and the 10-hydroxy-camptothecin nano particles 5 mg/kg treatment group, it was confirmed that both groups exhibit the max. IR after 2 or 3 days from the administration (d18). The max. IR of the CPT-11 treatment group was 69.0% (effective), and the 10-hydroxy-camptothecin nano particles treatment group was 85.4% (significant effect). By the t-test regarding the estimate tumor volume, 10-hydroxy-camptothecin nano particles treatment group was advantageous by p<5% of statistical significance. Although no statistical significance was observed on the final day of the experiment (d35), the IR of the CPT-11 treatment group was 8.9%, whereas the 10-hydroxy-camptothecin nano particles treatment group was 19.4%, which meant that the 10-hydroxy-camptothecin nano particles treatment group exceeded the CPT-11 treatment group.

Even the 10-hydroxy-camptothecin nano particles 2.5 mg/kg treatment group exhibited max. IR of 76.4% on d18, which was nearly "significant effect", and the tumor weight IR on the final day of the experiment (d35) was 25.5%, which was higher than that of the CPT-11 60 mg/kg treatment group.

Conclusion

Figure 20:
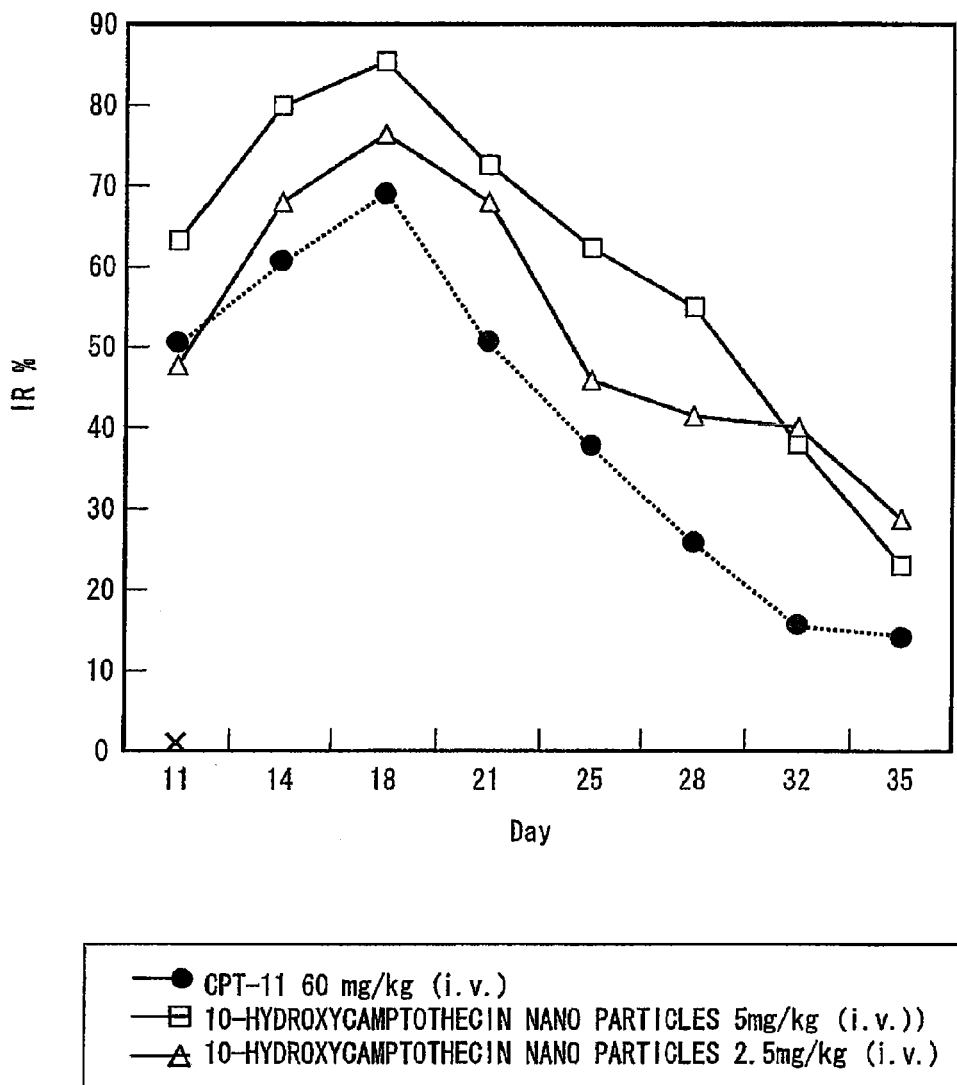
FIG. 20 is a graph showing the anti-tumor effects of 10-hydroxy-camptothecin nano particles and irinotecan hydrochloride (CPT-11), using human tumor tissue transplanted into nude mice.

From the studies of the anti-tumor effect using nude mice-transplanted human gastric cancer H-23, it was found that the tumor proliferation inhibiting effect of the 10-hydroxy-camptothecin nano particles treatment groups was advantageous over that of the CPT-11 treatment group (see FIG. 20).

INDUSTRIAL APPLICABILITY

The water- or alcoholic solution-insoluble anti-cancer drug in the form of ultrafine particles according to the present invention, and the complex of the same with a polymer electrolyte, are usable as an injection in which bioavailability is improved, and side-effects are suppressed.

Therefore, the present invention is expected to be applied to therapy for targeting specific tissues, using a polymer electrolyte which recognizes adhesion factors or any other specific cell tissue surface.

Further, by the present invention, it is expected that an anti-cancer agent can be outwardly effused over a long period, so as to suppress adverse side-effects caused when a drug is introduced into a body at once in a large amount.

Furthermore, the present invention can be expected to provide a safe and effective cancer therapy in which the drug is prepared to have a particle size within the range of 50 to 200 nm. Therefore, the drug can be selectively taken in by tumor cells with an enhancement permeability and retention (ERP) effect.

What is claimed is:

1. A method of producing water-insoluble anti-cancer drug in the form of particulates, the method comprising:
preparing a water-insoluble anti-cancer drug comprising a camptothecin derivative; and
irradiating said water-insoluble anti-cancer drug with a laser beam having a wavelength in a range of 420 to 430 nm such that said water-insoluble anti-cancer drug is formed into particulates having an average particle diameter of 50 to 200 nm.

2. The method according to claim 1, wherein the laser beam has an excitation light intensity in a range of 30 to 300 mJ/cm$^2$.

3. The method according to claim 1, further comprising coating the particulates of the water-insoluble anti-cancer drug with a polymer electrolyte such that the particulates of the water-insoluble anti-cancer drug form particulate complexes with the polymer electrolyte.

4. The method according to claim 3, wherein the coating of the particulates of the water-insoluble anti-cancer drug with the polymer electrolyte comprises subjecting the particulates of the water-insoluble anti-cancer drug to one of an electrostatic interaction and a hydrophobic interaction with the polymer electrolyte.

5. The method according to claim 1, wherein the preparing of the water-insoluble anti-cancer drug comprises suspending the water-insoluble anti-cancer drug in a liquid.

6. The method according to claim 3, wherein the coating of the particulates of the water-insoluble anti-cancer drug with the polymer electrolyte comprises forming the particulates of the water-insoluble anti-cancer drug into the particulate complexes having an average diameter of 50 to 250 nm.

7. The method according to claim 3, wherein the preparing of the water-insoluble anti-cancer drug comprises preparing a suspension comprising the water-insoluble anti-cancer drug and the polymer electrolyte prior to the irradiating of the water-insoluble anti-cancer drug.

8. The method according to claim 3, wherein the polymer electrolyte is at least one member selected from the group consisting of protamine, gelatin A, collagen, albumin, casein, chitosan, poly-(L)-lysine, carboxymethyl cellulose, alginate, heparin, hyaluronic acid, chondroitin sulfate, gelatin B, carageenan, dextran sulfate, poly-(L)-glutamic acid, polymethacrylic acid, and polydiaryldimethylammonium.

9. The method according to claim 3, wherein the preparing of the water-insoluble anti-cancer drug comprises preparing a suspension comprising the water-insoluble anti-cancer drug and the polymer electrolyte prior to the irradiating of the water-insoluble anti-cancer drug, and the polymer electrolyte has a concentration of 1 to 10% in the suspension.

* * * * *

UNITED STATES PATENT AND TRADEMARK OFFICE
CERTIFICATE OF CORRECTION

PATENT NO. : 8,399,024 B2
APPLICATION NO. : 12/879413
DATED : March 19, 2013
INVENTOR(S) : Hiroyuki Kato et al.

It is certified that error appears in the above-identified patent and that said Letters Patent is hereby corrected as shown below:

On the title page, Item (30), the Foreign Application Priority is incorrect. Item (30) should read:

--(30)            Foreign Application Priority Data

May 15, 2006   (JP)......................................................... 2006-135677--

Signed and Sealed this
Fourth Day of June, 2013

Teresa Stanek Rea
*Acting Director of the United States Patent and Trademark Office*